US010500355B2

(12) United States Patent
Holakovsky et al.

(10) Patent No.: US 10,500,355 B2
(45) Date of Patent: Dec. 10, 2019

(54) SYSTEM COMPOSED OF INHALER AND CAPSULE

(71) Applicant: Boehringer Ingelheim International GmbH, Ingelheim am Rhein (DE)

(72) Inventors: Holger Holakovsky, Witten (DE); Jessica Frentzel-Beyme, Gau-Algesheim (DE); Stephen Terence Dunne, Ipswich (GB); Jens Besseler, Bingen am Rhein (DE); Claudius Weiler, Ingelheim-Grosswinternheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1378 days.

(21) Appl. No.: 14/402,507

(22) PCT Filed: May 17, 2013

(86) PCT No.: PCT/EP2013/060272
§ 371 (c)(1),
(2) Date: Nov. 20, 2014

(87) PCT Pub. No.: WO2013/174752
PCT Pub. Date: Nov. 28, 2013

(65) Prior Publication Data
US 2015/0136131 A1    May 21, 2015

(30) Foreign Application Priority Data
May 21, 2012    (WO) ................. PCT/EP2012/059324

(51) Int. Cl.
*A61M 15/00*    (2006.01)
*B65D 47/28*    (2006.01)
(Continued)

(52) U.S. Cl.
CPC .... *A61M 15/0035* (2014.02); *A61M 15/0025* (2014.02); *A61M 15/0028* (2013.01);
(Continued)

(58) Field of Classification Search
CPC .......... A61M 15/0025; A61M 15/0028; A61M 15/003; A61M 15/0031; A61M 15/0033;
(Continued)

(56) References Cited

U.S. PATENT DOCUMENTS

| 4,076,848 A | 2/1978 | de Limur |
| 4,889,114 A | 12/1989 | Kladders |

(Continued)

FOREIGN PATENT DOCUMENTS

| DE | 102004040928 A1 | 3/2006 |
| EP | 0666085 A1 | 8/1995 |

(Continued)

*Primary Examiner* — Kendra D Carter
*Assistant Examiner* — Elliot S Ruddie
(74) *Attorney, Agent, or Firm* — Matthew B. Dernier, Esq.

(57) ABSTRACT

The invention relates to a system composed of an inhaler and a capsule, preferably intended for single use. The capsule contains a preferably powdered pharmaceutical preparation which, for inhalation, is expelled from the capsule through at least one hole. The capsule comprises as capsule elements a capsule cap and a capsule body, at least one of which comprises at least one prefabricated hole. The prefabricated hole in the capsule is sealed off in the transporting state of the system and is open in the usage state. The hole is exposed by actuation of a pulling mechanism. Prior to this the hole is closed off by a capsule receptacle or a film.
In one embodiment the capsule may be present in two different states, for example in different insertion positions of the capsule elements. In the first state the prefabricated hole is closed off and in the second it is exposed.

(Continued)

Also shown is an inhaler suitable as a disposable product, which is manufactured from thermoformed parts or from blister film.

28 Claims, 7 Drawing Sheets

(51) Int. Cl.
 *A61J 3/07* (2006.01)
 *A61K 9/00* (2006.01)
(52) U.S. Cl.
 CPC .... *A61M 15/0043* (2014.02); *A61M 15/0086* (2013.01); *B65D 47/283* (2013.01); *A61J 3/071* (2013.01); *A61K 9/0075* (2013.01); *A61M 15/0071* (2014.02); *A61M 15/0081* (2014.02); *A61M 2202/064* (2013.01)
(58) Field of Classification Search
 CPC .......... A61M 15/0035; A61M 15/0043; A61M 15/0061; A61M 15/0063; A61M 15/0086; A61M 15/0071; A61M 15/0081; A61M 2202/064; B65D 47/283; B65D 49/12; A61J 3/07; A61J 3/071; A61J 3/072; A61J 3/074; A61J 3/077; A61K 9/0075
 See application file for complete search history.

(56) References Cited

U.S. PATENT DOCUMENTS

| | | | |
|---|---|---|---|
| 5,152,284 A | 10/1992 | Valentini | |
| 5,170,801 A | 12/1992 | Casper | |
| 5,498,255 A | 3/1996 | Wong | |
| 5,673,686 A * | 10/1997 | Villax | A61M 15/0028 128/203.12 |
| 6,418,926 B1 | 7/2002 | Chawla | |
| 7,025,057 B2 | 4/2006 | Chawla | |
| 7,249,600 B2 | 7/2007 | Chawla | |
| 7,305,986 B1 | 12/2007 | Steiner | |
| 7,878,193 B2 | 2/2011 | Kladders | |
| 8,434,477 B2 | 5/2013 | De Vos | |
| 8,662,076 B2 | 3/2014 | Kuehn | |
| 9,010,325 B2 | 4/2015 | Djupesland | |
| 2001/0008637 A1* | 7/2001 | Hochrainer | A61J 3/071 424/451 |
| 2004/0131668 A1 | 7/2004 | Hochrainer et al. | |
| 2004/0173211 A1 | 9/2004 | Kladders et al. | |
| 2006/0157054 A1 | 7/2006 | Kuehn | |
| 2007/0029768 A1 | 2/2007 | Clos | |
| 2007/0151562 A1 | 7/2007 | Jones | |
| 2007/0163581 A1 | 7/2007 | Braithwaite | |
| 2008/0177246 A1 | 7/2008 | Sullivan | |
| 2009/0194105 A1 | 8/2009 | Besseler et al. | |
| 2009/0241949 A1 | 10/2009 | Smutney | |
| 2009/0308392 A1 | 12/2009 | Smutney | |
| 2010/0132705 A1 | 6/2010 | De Vos | |
| 2010/0300439 A1* | 12/2010 | Djupesland | A61M 15/0028 128/203.15 |
| 2013/0042864 A1* | 2/2013 | Adler | A61M 15/0028 128/203.15 |

FOREIGN PATENT DOCUMENTS

| | | |
|---|---|---|
| FR | 1215560 A | 4/1960 |
| FR | 2032436 A2 | 7/1980 |
| GB | 1396258 A | 6/1975 |
| JP | 49130094 A | 12/1974 |
| JP | 0623020 A | 2/1994 |
| JP | 07222800 A | 8/1995 |
| JP | 2000217920 A | 8/2000 |
| JP | 2003508165 A | 3/2003 |
| JP | 2006517421 A | 7/2006 |
| JP | 2006521958 A | 9/2006 |
| JP | 2010512832 A | 4/2010 |
| WO | 200172605 A1 | 10/2001 |
| WO | 2004062640 A2 | 7/2004 |
| WO | 2004062716 A1 | 7/2004 |
| WO | 2006074982 A2 | 7/2006 |

\* cited by examiner

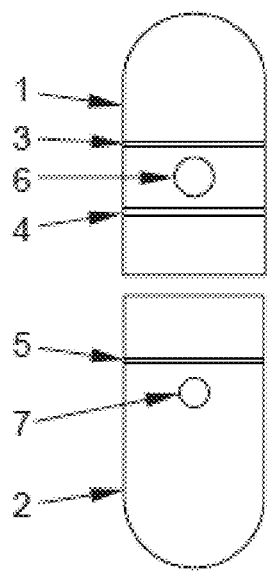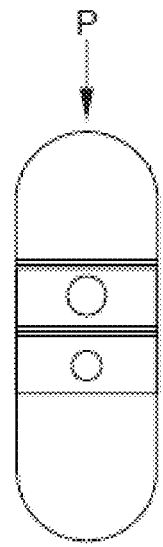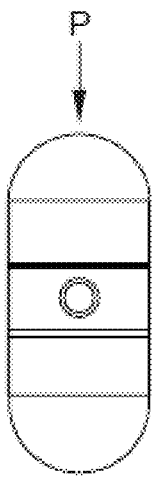
FIG. 1a     FIG. 1b     FIG. 1c
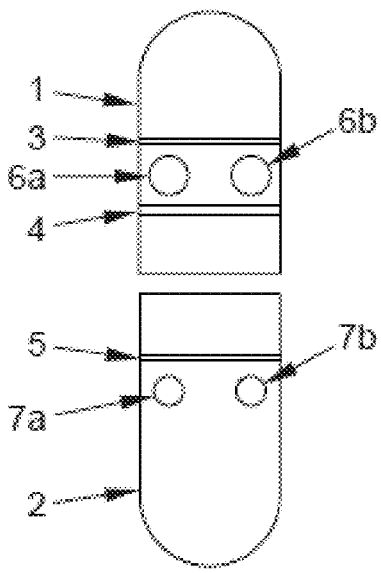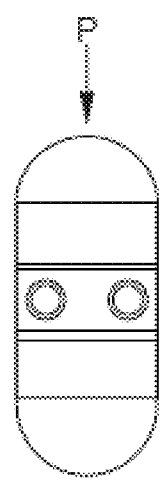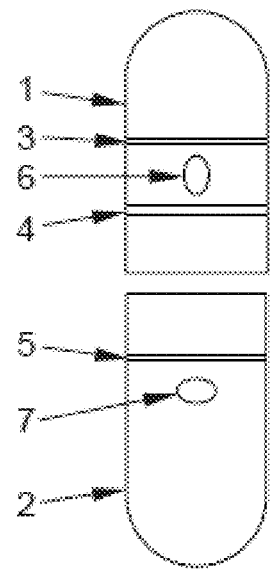
FIG. 2a     FIG. 2b     FIG. 3
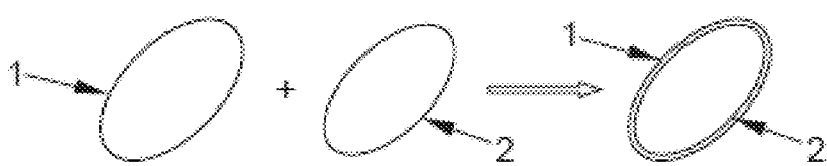
FIG. 4
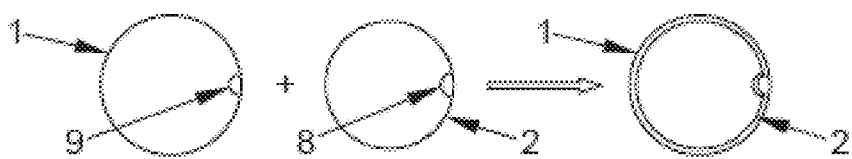
FIG. 5

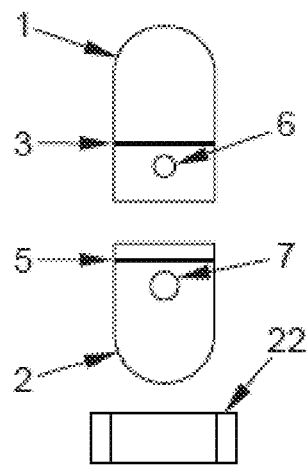 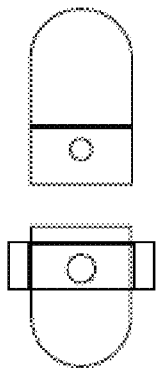 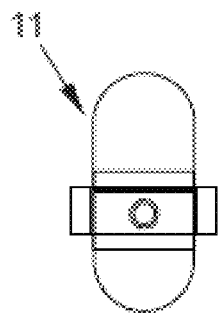
Fig. 6a Fig. 6b Fig. 6c
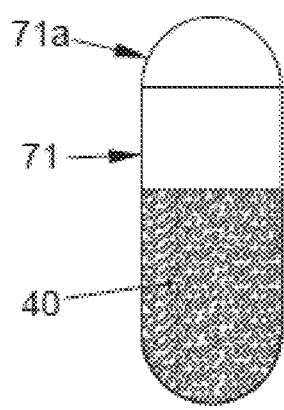 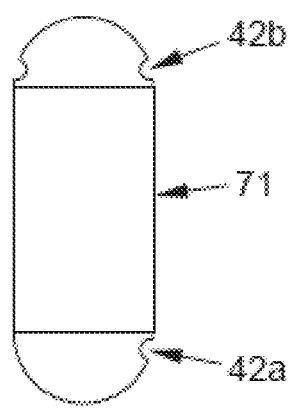 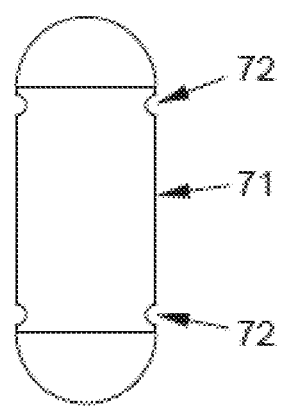
Fig. 7a Fig. 7b Fig. 7c

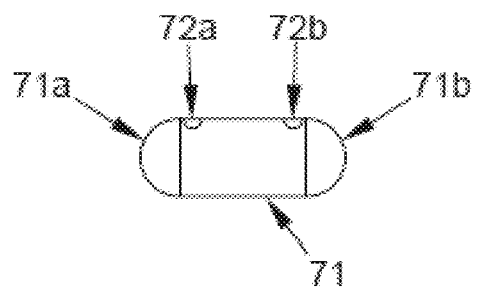
Fig. 8a
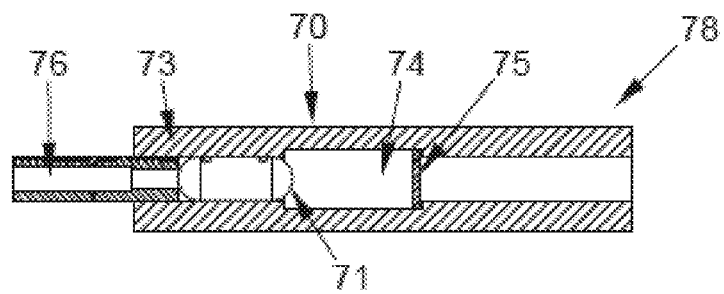
Fig. 8b
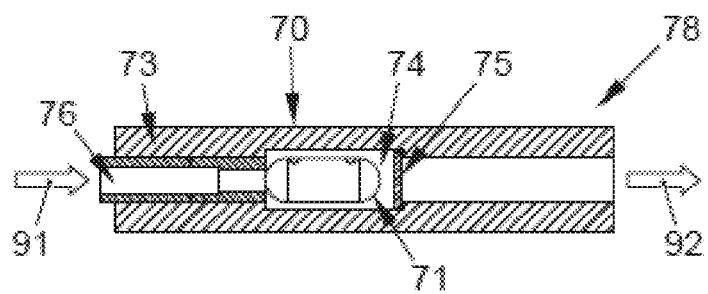
Fig. 8c
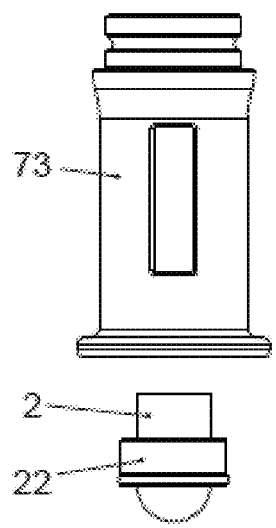 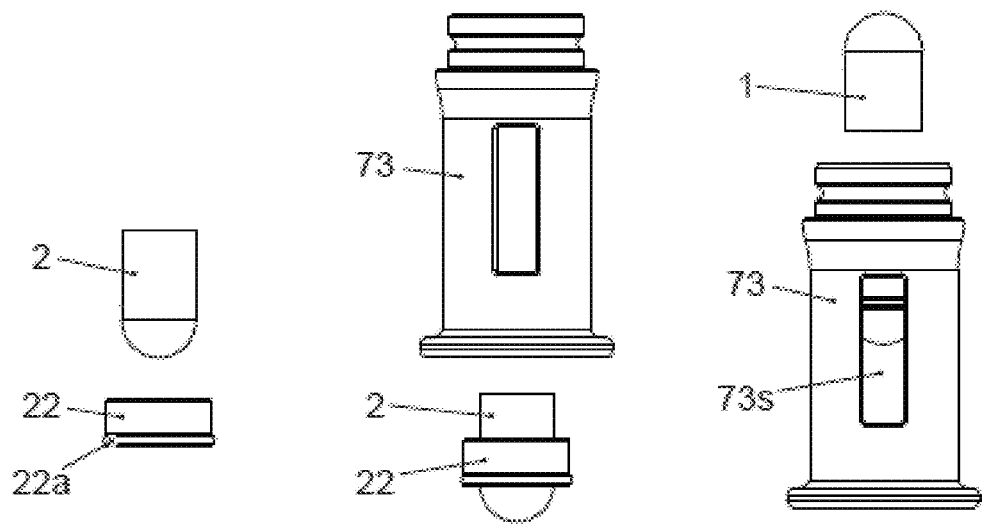 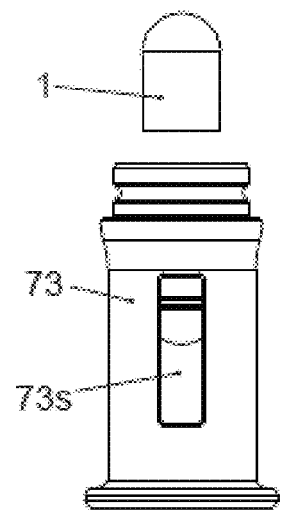
Fig. 9a  Fig. 9b  Fig. 9c

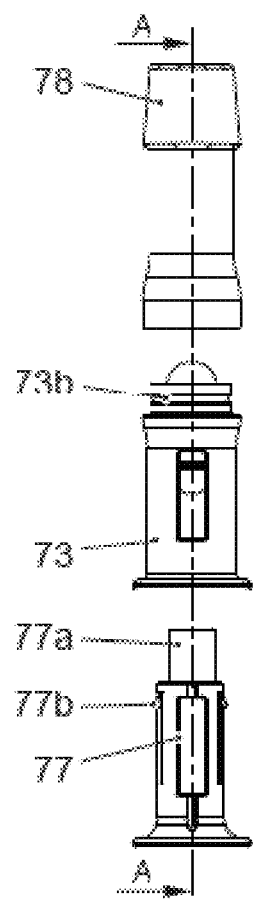
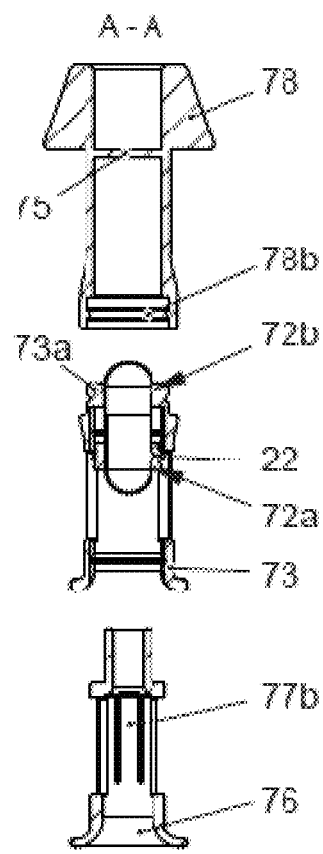
Fig. 9d   Fig. 9e
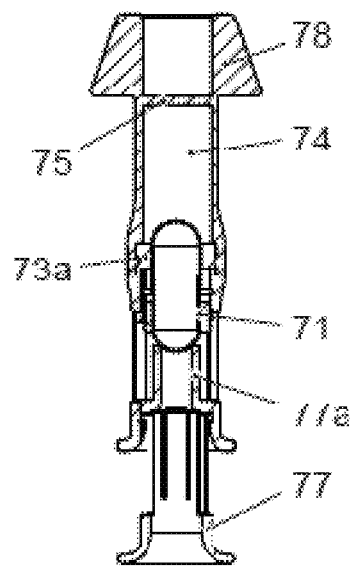
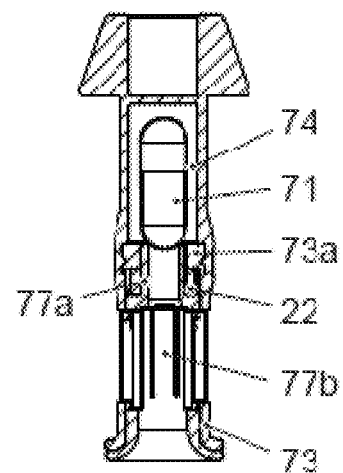
Fig. 9f   Fig. 9g

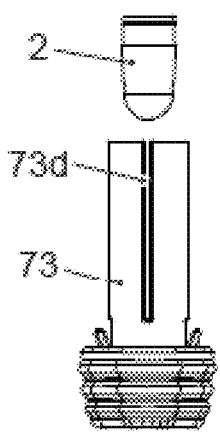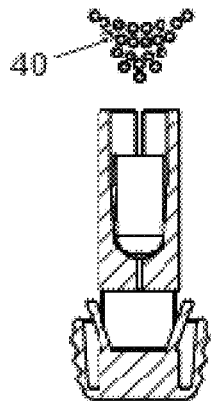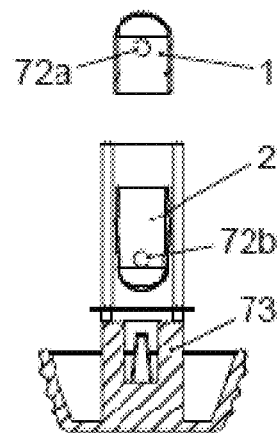
Fig. 10a　　　Fig. 10b　　　Fig. 10c
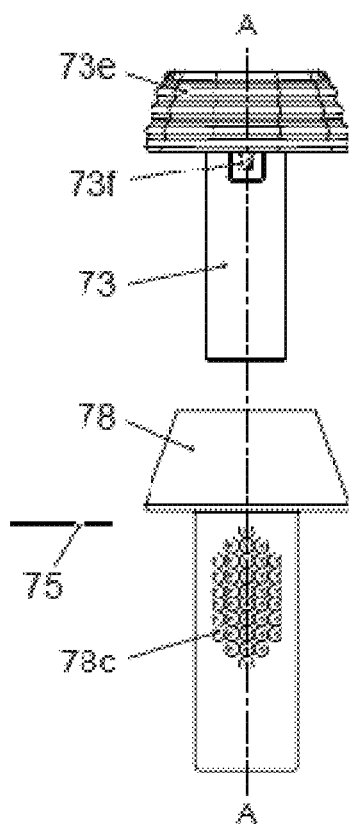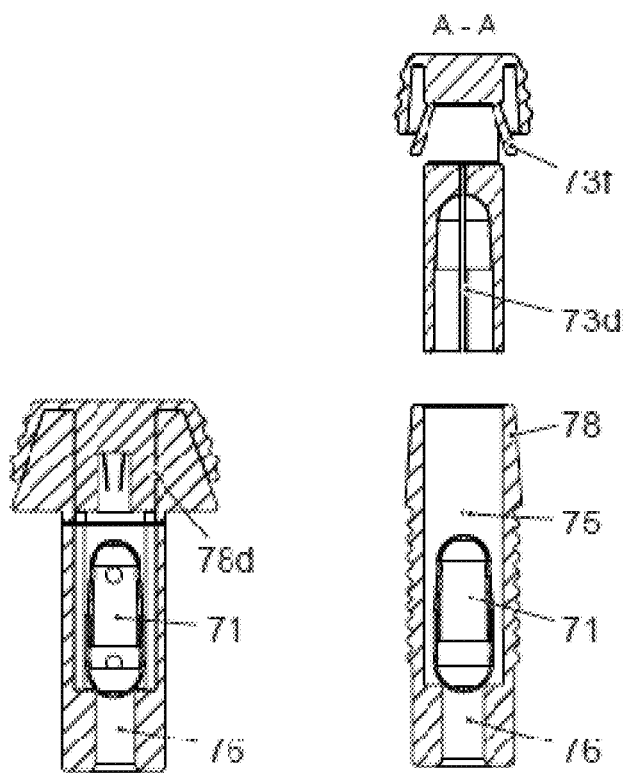
Fig. 10d　　　Fig. 10e　　　Fig. 10f

SYSTEM COMPOSED OF INHALER AND CAPSULE

This application is the national phase entry under 35 U.S.C. § 371 of International Application No. PCT/EP2013/060272, filed May 17, 2013, which claims priority to pct/ep2012/059234, filed May 21, 2012, the contents of which are hereby incorporated by reference in their entireties.

The present invention relates to a system composed of a capsule for holding medicinal formulations for use in an inhaler and an associated inhaler. In particular the invention relates to systems comprising capsules that are filled with a powdered pharmaceutical preparation and to inhalers with which a powdered pharmaceutical preparation is to be provided for inhalation, the powder being contained in a capsule and being expelled from the capsule for inhalation through at least one hole in the capsule wall.

Capsules are known from the prior art that are used in specific medical devices such as powder inhalers. The outer shape of capsules used in inhalers of this kind is often (as in the present specification) that of a closed cylinder with hemispherical ends, the length of the cylinder being greater than its diameter. Such capsules usually consist of two cup-shaped parts, namely a capsule body and a capsule cap which are fitted telescopically into one another. Various materials are known for such capsules. Many capsules used in medicine consist of gelatine or hard gelatine.

WO2000/07572 discloses plastic capsules for use in powder inhalers. The capsules consist of a capsule cap and capsule cap which may be jointed together so as to form a stable sealed cavity of a defined volume. The capsule may comprise latching elements that securely connect the capsule cap to the capsule body. An example of latching elements of this kind are dot-like elevations in the inner casing of the capsule cap, which engage in rather larger dot-shaped depressions on the outer casing of the capsule body. The capsule cap and capsule body both consist of the same water-insoluble, hydrophobic plastics, preferably polyethylene.

WO2006/074982 A2 discloses a closure concept for capsule cap and capsule body by means of which it is possible to join the two parts together temporarily for transporting the capsule to the filling apparatus, by means of a preliminary closure which, unlike the main closure, can be opened non-destructively. The closures are formed in the inner casing of the capsule cap by annularly extending or segment-shaped elevations and matching depressions arranged annularly around the periphery of the outer casing of the capsule body.

Various powder inhalers are known from the prior art, in which the powder is contained in capsules before inhalation. In these devices the capsules are generally opened in some way to give access to the powder for nebulisation: in some devices the capsules are cut open with cutting blades, while in others their interior is brought into communication with air passages in the inhaler by means of hollow needles. In one group of inhalers that particularly form the background to the present invention, holes are pierced in the capsules by means of needle devices.

WO2004/082750 A1 shows an example of such an inhaler in which a capsule is pierced at both ends by two opposing needles. During the inhalation process the capsule rotates about its transverse axis, being driven by air flowing in tangentially. Particles that are driven out of the interior of the capsule by its rotation then travel through the air current to the mouthpiece.

U.S. Pat. No. 5,896,855 shows an inhaler in which a plurality of capsules are stored in a rotatable magazine and are supplied by a selectively motor-controlled mechanism to a spin chamber, where the powder is also expelled from holes at the ends of the capsule by rotation of said capsule. In the magazine, the capsules are held at both ends by needles or stoppers. The capsules are either pierced at their polar ends before they are inserted in the magazine and these holes are closed up by the stoppers in the magazine until the capsule in question is delivered to the spin chamber; or the capsules are pierced by these very needles as the capsules are inserted in the magazine and the piercing needles remain in the holes to form a seal until the capsule in question is delivered to the spin chamber.

WO04/052435 A1 shows different capsule-based powder inhalers in which the nebulisation takes place using the so-called Bernoulli effect. One inhaler shown has a mouthpiece which is of similar configuration to a cap and on which a lower part is fitted which contains a capsule chamber. On the lower housing part is provided a cutting device for opening the capsules. To replace the used capsules with new ones, the mouthpiece is flipped up or a plug-in connection is released which is located between the mouthpiece and lower housing part or between the mouthpiece and a plate inserted in the lower housing part and connected to the capsule chamber. Another inhaler shown has a rotatably mounted, exchangeable or refillable revolver magazine having a plurality of chambers each loaded with a capsule.

Powder inhalers of this kind using the Bernoulli effect constitute the starting point for the invention described here and the mode of operation described hereinafter also applies to the inhalers which are the subject of the present inventions.

In the inhalers under discussion here, the active substance that is to be delivered is stored in a substantially cylindrical capsule and this capsule is inserted in the inhalation chamber of an inhaler. The capsule chamber is adapted to the size of the capsule so that it is also substantially cylindrical in configuration, its length and diameter being somewhat greater than the corresponding dimensions of the capsule. As a result the capsule inserted in the capsule chamber has enough clearance to enable it to perform vibratory movements in both the axial and radial direction, while nevertheless remaining substantially aligned along the chamber axis. The capsule chamber comprises an air inlet in the region of one of its two ends and an air outlet opening in the region of the other end. The air outlet is attached to an inhalation channel which leads to the mouthpiece of the inhaler. As a rule, the capsule chamber, air outlet, inhalation channel and opening in the mouthpiece are arranged along a common axis.

In order to deliver the contents of the capsule, the capsule is first opened normally at two points along the length of the casing. As a rule the openings are located close to the two longitudinal ends of the capsule. If an air current is then generated in the capsule chamber from the air inlet to the air outlet, this leads along the longitudinal axis of the capsule and has two effects: on the one hand, the capsule vibrates, with its preferable direction of movement running along the longitudinal axis as a result of the air current. On the other hand, the air flowing along the two capsule openings generates a negative pressure relative to the capsule interior, so that the powder contained in the capsule is sucked out by the air current and thereby nebulised.

The problem on which the present invention is based is to provide a system composed of a capsule and inhaler which is an improvement on the prior art, in which the reproducibility of the nebulisation, particularly the expulsion of powder from the capsule, is improved. Preferably, a system is to be provided in which irregularities in the opening of the capsules are reduced or minimised. Particularly preferably, a system and an inhaler are to be provided which are suitable for single use or for use as a disposable system or disposable product.

This problem is solved according to the invention by a system composed of an inhaler and a capsule according to claim 1 and a method for assembling a system of this kind according to claim 21 and an inhaler according to claim 24.

One feature of the system according to the invention which is formed by a capsule and an inhaler is that the inhaler comprises a capsule chamber and before the inhaler is used the capsule is stored in a capsule receptacle belonging to the system or to the inhaler. The capsule is used as a reservoir for a pharmaceutical preparation or medicinal formulation and comprises two capsule elements open at one end, namely a capsule body and a capsule cap, which can be fitted telescopically into one another through their openings to form a cavity. The capsule body and capsule cap are characterised in that at least one of the two, and preferably both, have at least one prefabricated hole in addition to the opening at one end.

The capsule receptacle seals off at least one hole and/or all the holes that lead(s) into the cavity of the capsule after the capsule elements have been fitted together. The capsule receptacle is arranged at least partially in the capsule chamber and can be removed from the capsule chamber in such a way that the capsule is left behind in the capsule chamber when the capsule receptacle is removed.

Another feature of the present invention is that a capsule filled with a pharmaceutical preparation which comprises a capsule cap and/or a capsule body with prefabricated holes is used in an inhaler, the prefabricated holes being covered at the moment of insertion of the capsule in a capsule chamber of the inhaler and being exposed by the actuation of a pulling element in the inhaler.

This makes it possible to provide a capsule-based inhaler preferably using the Bernoulli effect for nebulisation, in which no piercing devices have to be provided to perforate the capsule. The exposing of prefabricated holes offers various advantages over the use of piercing means in the inhaler: as a result of the manufacturing process, e.g. by plastics extrusion, the prefabricated holes are highly reproducible in size and shape from one capsule to another, whereas holes produced by piercing may vary individually depending on the capsule material, capsule size and equipment as well as the piercing position and geometry of the needles, and/or may lead to irregular hole geometries. Moreover, when capsules are pierced, it is possible for a certain spring-back to occur in the capsule surface in the region of the piercing site. The prefabricated holes envisaged here, by contrast, are stable in shape after being exposed and have no protrusions in the capsule material. Such protrusions in the capsule material are formed for example when the capsule wall is pressed in by a piercing device and may possibly lead to the accumulation of, in particular, powdered pharmaceutical preparation and hence to a slightly reduced delivery of the preparation from the capsule on nebulisation. Because of the high precision in the size and shape of the capsule holes which is made possible by the prefabrication of the holes, both the amount and also, in particular, the distribution of the powder expelled from capsules in the airflow in the capsule chamber of an inhaler are more reproducible. The nebulisation of the pharmaceutical preparation itself is thus made more reproducible, particularly compared with inhalers having capsule piercing means.

Another feature of the present invention is that the inhaler for use with capsules having prefabricated hole comprises a pulling element and for actuating the pulling element channels or openings are used, which are required in any case on account of the operating principle of the inhaler. This means, in particular, that the pulling element is arranged in an air channel of the inhaler. For opening the capsule, therefore, no additional openings need to be formed on the capsule chamber which might adversely affect the flow characteristics during nebulisation. There is no formation of unwanted secondary air or false air besides the air channels required for the nebulisation. The system is stable and reproducible in terms of the flow resistance.

By comparison, when using a piercing device, the associated piercing element has to be introduced into the capsule chamber through one or more openings, which may lead to additional unwanted air flow through these openings during inhalation. Such openings in addition to an air inlet and air outlet for the capsule chamber are not needed in the inhaler according to the invention, if they are not in turn designed to improve the airflow in the capsule chamber.

The use of a pulling element to expose prefabricated holes has an additional advantage, over the use of piercing elements: when using piercing elements, as a result of the clearance required for movement of the capsule in the capsule chamber that is necessary for the nebulisation process, there may be fluctuations in the position of the capsule relative to the piercing tips when the capsule is pierced in the capsule chamber. Compared with numerous similar capsule-inhaler systems this leads to fluctuations in the exact position of the holes in the respective capsule.

As a result of the use of a pulling mechanism for exposing prefabricated holes on capsules, all the fluctuations in the shape, size and position of the holes resulting from the use of piercing devices and the consequent fluctuations in the delivery of the pharmaceutical preparation are avoided. The nebulisation of the pharmaceutical preparation is then independent of the mechanism for opening the holes in the capsule. This also means that when brittle capsule material is used, the risk of splintering, which may occur particularly in piercing processes, is minimised. In this way the range of possible capsule materials for use in inhalers is widened.

The use of a pulling mechanism for exposing prefabricated hole has the additional advantage, depending on the configuration of the pulling element, that the same mechanism can be used to expose all kinds of hole arrangements on capsules. For example, in cylindrical arrangements of capsule, capsule chamber and pulling element, there may be a plurality of holes on the capsule at different locations relative to its circumference. The size, shape, position and number of holes in a capsule are very variable in this design, particularly when the capsule parts are produced by injection moulding processes. Here, the results of flow simulations matched to the nebulisation of specific pharmaceutical preparations or specific powders may be used to make use of optimum hole structures for capsules for this particular preparation or this particular powder.

A further feature of the invention, which may also be applicable to inhalers in general, independently of the other features of the invention, is that the inhaler comprises a body (100) which forms a chamber such as, in particular, a vibration chamber of preferably a capsule chamber (74) for holding a preferably powder-filled capsule (71), and the material of this body (100) consists essentially of a thermoformed film or a blister film. The use of materials of this kind which have been well researched in the field of the packaging of medicinal tablets with regard to their compatibility with medicinal active substances allows for very cheap production of inhalers which would otherwise be manufactured at greater cost in materials, e.g. by plastics extrusion moulding.

Preferably, the body is formed from two halves or parts which are joined together by sealing, laminating, gluing or welding. Preferably, the reservoir which contains a medicinal preparation that is to be nebulised or expelled, or particularly, as is preferred here, a capsule receptacle containing a powder-filled capsule, is placed in the chamber before the two halves or parts of the body are joined together. This process consisting of just a few operating steps makes for an uncomplicated and hence quick and inexpensive assembly process. As a result of the manufacturing costs which are reduced overall, compared with the production of standard commercial inhalers, the inhalers thus produced from thermoformed parts are highly suitable for use as one way inhalers, i.e. as products for single use or as so-called disposable items.

In addition, the principle of the inexpensive assembly of two inhaler parts which form an inner chamber, preferably for an enclosed object, can also be applied to components produced by plastics extrusion (instead of thermoformed components): Two such components can be joined together along their connecting surfaces by ultrasound welding, for example.

Advantageous further features are described hereinafter and in detail by reference to the drawings.

In one embodiment, the at least one hole prefabricated in the capsule is closed off by a pulling element, the pulling element forming a capsule receptacle, or a capsule receptacle is part of the pulling element. This capsule receptacle is substantially in the shape of a cylindrical tube which is of such dimensions as to fit exactly around the cylindrical part of the capsule. The at least one prefabricated hole in the capsule is located in the cylindrical casing region of the capsule and is thus closed off by the wall of the capsule receptacle while the capsule is being stored or held in the inhaler. Preferably, the powder-filled capsule stored in this way has two holes at top and bottom, i.e. one hole at the start and one at the finish of the cylindrical casing region. Preferably, the capsule consists of a capsule body and a capsule cap, both of which have at least one prefabricated hole, while after the capsule body and capsule cap have been pushed into one another the holes remain exposed, i.e. not covered by the respective other capsule element. Alternatively the holes may also be prefabricated after the filling of the capsule and after the assembly of the capsule cap and capsule body outside the inhaler. In the capsules, amounts of powder of between 0.1 milligrams and 100 milligrams of a pure active substance or an active substance mixture may be stored, for delivery later.

In a preferred embodiment of the system according to the invention, the system of inhaler and capsule, particularly in the case of a system for one-time use (single-use system), this system comprises a pulling mechanism for exposing the prefabricated capsule holes. The pulling mechanism is preferably constructed so that the capsule is located in a capsule receptacle and the capsule receptacle is located in the capsule chamber in a state of the system suitable for transporting and storage. To make the system ready for use, the capsule receptacle is pulled out of the capsule chamber, preferably also pulled completely out of the inhaler. A device is provided which prevents the capsule with the capsule receptacle from being pulled out of the capsule chamber and/or prevents the capsule from being released from the capsule receptacle when the capsule receptacle is pulled out.

Preferably, the capsule receptacle is pulled out through a mouth tube on the inhaler. The mouth tube forms the air outlet from the capsule chamber towards the mouth end of the inhaler. This device for retaining the capsule in the capsule chamber preferably contains a bar or crosspiece which at the same time forms the upper boundary of the capsule chamber. This bar or crosspiece preferably passes through the capsule receptacle, in the storage state of the system, on the side opposite an air inlet of the capsule chamber. The capsule receptacle preferably comprises slot-like recesses as a result of which the capsule receptacle is able to slide past the crosspiece as it is pulled out of the inhaler and thus be separated from it.

Preferably, the component forming the capsule receptacle in the transporting state of the system comprises a region protruding from the inhaler, on which is formed a gripping surface which the user can grasp in order to pull the capsule receptacle out of the inhaler. Also particularly preferably the component forming the capsule receptacle is configured as a cap which covers the mouth end of the inhaler in the transporting state.

The capsule receptacle or the pulling element by means of which the holes are sealed off or exposed is designed as a function of the sealing concept of the prefabricated holes in the capsule. In a preferred embodiment, the capsule receptacle is formed by the pulling element. Preferably, the capsule receptacle and pulling element are produced as one or more thermoformed components from a blister film. Preferably, the capsules in the capsule receptacle are sealed in the region of the prefabricated holes by a sealing process at the pulling element. Preferably, the capsule receptacle is flexibly arranged such that the capsule can be released from the capsule receptacle non-destructively by pressure along the longitudinal axis of the pulling element; for example, as described above, by the capsule being held back by a bar or other obstacle as the pulling mechanism is actuated while the capsule receptacle can slide past the bar or obstacle by means of a suitable slot.

Another feature of the invention is that in the case of systems for single use, the components involved in the respective pulling mechanism comprise devices that ensure that the respective pulling movement cannot be reversed non-destructively. In particular, the pusher or the capsule receptacle comprises for this purpose spring arms or other elements which, in the event of the capsule receptacle being pulled out, prevents the capsule receptacle from being non-destructively returned to the capsule chamber.

The systems described above for single use may alternatively also be designed as systems with two capsules. In embodiments of this kind for two capsules the inhaler also comprises two associated two capsule chambers and two capsule receptacles. Depending on the intended use of a system of this kind having two capsules, the two capsules are optionally filled with different formulations and/or different amounts of formulation. A system of this kind comprising an inhaler and two capsules may be used for example in therapies in which two different medical formulations have to be administered simultaneously to a patient. With capsules having different fillings it may be useful to tailor the size of the capsules to the respective amount of filling. In a very particular embodiment of this kind the respective capsule chambers and capsule receptacle are also adapted in size to the respective capsules. Irrespective of the fact that this is an embodiment with two identical or two different capsules, in a system of this kind with two capsules the pulling mechanism on the inhaler is configured so that with one movement the holes on both capsules are exposed simultaneously. If the system comprises capsule receptacles for example that extend in mouth tubes of the inhaler, and a cap with a gripping surface or a tab for pulling, when the cap is pulled the two capsule receptacles preferably joined together in the region of the cap are pulled out of the inhaler simultaneously.

In another embodiment of a system according to the invention, the system is formed from an inhaler and an assembled capsule with at least one prefabricated hole, the capsule being in the inhaler in the portable state of the system and thus at least partially surrounded by a preferably extensible and/or flexible film such that the film closes off the at least one prefabricated hole and/or all the holes in the capsule in the portable state of the system. The film is preferably connected to a pull strip or other gripping element and/or projects partially beyond the capsule at one end of the capsule (the film with the pull strip or the protruding film itself is therefore the "pulling element" in these embodiments). The inhaler comprises an opening through which the film can be pulled out of the inhaler at its projecting portion and/or at its pull strip, thereby exposing the prefabricated holes on the capsule.

Because of the low complexity of a system based on a pull mechanism and the associated low manufacturing costs, a system of this kind comprising a capsule with prefabricated, initially covered holes and a capsule receptacle or pulling element inserted into a capsule chamber, is also suitable for the production of single dose inhalers (disposable items). Particularly in applications where sticky, powdered pharmaceutical preparations are to be provided for inhalation, deposits rapidly form in the capsule chamber, air outlet and mouthpiece, so that frequent changing of such a system is desirable, as by using a disposable product.

In one embodiment of the system composed of inhaler and capsule according to the invention, the assembled capsule may be present in two different states: in the first state, the at least one prefabricated hole is closed, and in the second, it is open.

Thus, the two capsule elements comprise prefabricated holes and, when fitted telescopically into one another, two insertion positions relative to one another (these two insertion positions correspond in their configuration to the so-called first and second states of the capsule): a first insertion position in which the two elements are fitted into one another such that the prefabricated holes are covered and the cavity of the capsule as a whole is closed off, and a second insertion position in which the prefabricated holes in the capsule body and capsule cap overlap with one another, such that the entire capsule has one hole at the place of overlap of the two holes.

Preferably, both capsule elements are cup-shaped: The cavity open at one end which they form is laterally bounded by a surrounding capsule casing and by a closed end relative to the open side. Preferably, the capsule casing forms a cylindrical or elliptically surrounding wall, so that no corners are formed on the inside of the assembled capsule in which, in particular, powdered pharmaceutical preparation could accumulate and thus be left behind when powder is subsequently expelled from the capsule. For the same reason, the undersides of the capsule body and capsule cap and hence both ends of the capsule produced by fitting them together have a convex, particularly substantially hemispherical or ellipsoid shape.

The prefabricated holes in the capsule cap and capsule body are preferably located in the respective casing area, so that when they are fitted together the casing of the other capsule element covers the respective hole until the insertion position in which the two holes are brought into registry is reached.

By the use of the term "prefabricated" for a hole is meant that the hole is produced in the respective capsule element during the capsule manufacturing process at the factory. The hole in the respective capsule element is already present before the individual capsule has been finally assembled. In particular, the hole or holes is or are already present in the capsule elements before the capsule as a whole is inserted in an inhaler.

Preferably, the capsule cap and capsule body are structured, on the sides of the capsule casing region that fit against one another in the assembled state. This structuring is preferably designed to perform different functions. On the one hand, the structures of the capsule cap and capsule body have alternate latching elements. Preferably, when the capsule elements are fitted into one another, this structure causes the capsule cap and the capsule body to latch together in relation to one another in at least two positions, particularly the insertion positions referred to. Latching in the first insertion position ensures that on the one hand the holes in the capsules are not accidentally exposed prematurely, e.g. as a result of vibration during transporting, and a defined process such as pushing the two elements together while applying a defined pressure is needed in order to expose the holes. Moreover, the cooperating latching elements of the capsule cap and capsule body are preferably configured so that after being fitted together up to the first insertion position the two capsule elements can no longer be non-destructively separated from one another. This prevents the capsule from opening accidentally. Preferably, in the contact region between the capsule cap and capsule body, structuring elements are also provided which serve as a guide for the two capsule elements as they are fitted into one another. These structuring elements on the casing regions of the capsule cap and capsule body that are directed towards one another ensure that the two capsule elements can only be fitted into one another in defined alignments. The "defined alignment" refers to the rotation of the capsule elements about the longitudinal axis of the capsule and is therefore an azimuthal alignment. Preferably, these structuring elements are in the form of at least one groove in the outer/inner casing surface of the capsule cap/capsule body and, respectively, in the form of at least one guide rail in the inner/outer casing surface of the capsule body/capsule cap. This ensures that when the capsule elements are fitted into one another the prefabricated holes in the capsule cap and capsule body are brought safely into registry. Preferably, the guides used are straight, particularly parallel to the main axis of the capsule. Variants in which the structuring elements guide the movement of the capsule elements along a curved path during the assembly are also possible. This would be achieved for example by a helical guide groove or guide rail.

Another feature of the present invention that may be implemented both independently and in conjunction with the above-mentioned aspects is that the capsule instead of being cylindrical in cross-section has an elliptical cross-section. Preferably the ellipse is one that deviates only slightly from the shape of a circle (the ratio of longitudinal to transverse axis of the ellipse should be less than 75%, preferably between 90% and 85%). An elliptical cross-section of this kind forces a defined azimuthal alignment of the two capsule elements as they are fitted together and/or a defined orientation when a resulting capsule is fitted into a capsule receptacle.

According to a further feature of the present invention, the hole in the outer capsule element is preferably configured as an oblong hole, or an elliptical hole or somewhat larger than the associated hole in the inner capsule element. When the outer hole is formed as an oblong hole or an ellipse, the small diameter of the hole is preferably at least as great as the diameter of the hole in the inner capsule element. The outer capsule element is the one that is formed by the outer wall of the capsule, by means of the capsule body and capsule cap in the assembled state in the region of the capsule casings abutting on one another. As a result of this enlargement of the outer hole relative to the inner one, the tolerances with respect to the accuracy of insertion of the capsule elements are broadened. This ensures that even if they are not pushed together precisely, the entire capsule opening is still available.

The individual features of the present invention may be used independently of one another or combined with one another.

Further advantages, features, properties and aspects of the present invention will become apparent from the claims and the following description of preferred embodiments by reference to the drawings. In the drawings:

FIG. 1 shows a schematic representation of a special capsule in different states: a) capsule cap and capsule body before being fitted together, b) capsule cap and capsule body in a first insertion position and c) capsule cap and capsule body in a second insertion position;

FIG. 2 shows a schematic representation of a second embodiment of the capsule in different states: a) capsule cap and capsule body before being fitted together, and b) capsule cap and capsule body in a second insertion position;

FIG. 3 shows a schematic representation of a third embodiment of the capsule, wherein the capsule cap and capsule body are shown before being fitted together;

FIG. 4 shows a schematic cross-section of a fourth embodiment of the capsule, wherein in the first half of the drawing the capsule cap and capsule body are shown before being fitted together and in the second half of the drawing the capsule cap and capsule body are shown after being fitted together.

FIG. 5 shows a schematic cross-section of a fifth embodiment of the capsule, wherein in the first half of the drawing the capsule cap and capsule body are shown before being fitted together and in the second half of the drawing the capsule cap and capsule body are shown after being fitted together.

FIG. 6 is a schematic representation of a sixth embodiment of the capsule according to the invention in different states: FIG. 6a shows the capsule cap, capsule body and ring before they are fitted together, FIG. 6b shows the capsule cap separated from the ring and capsule body that have been pushed together, and FIG. 6c shows the capsule cap and capsule body in a second insertion position.

FIG. 7 is a schematic representation of a seventh and an eighth embodiment of a capsule: FIG. 7a shows the closed capsule with filling, FIG. 7b shows the position of holes in the capsule according to the seventh embodiment and FIG. 7c according to the eighth embodiment.

FIG. 8 is a schematic representation of a ninth embodiment of the capsule according to the invention with the associated mode of operation of an inhaler with a pushing mechanism: FIG. 8a shows the capsule with prefabricated holes, FIG. 8b shows the capsule stored in an inhaler and FIG. 8c shows the capsule after being moved from its storage state into the capsule chamber of the inhaler.

FIG. 9 is a schematic representation of the mode of operation of a second embodiment of an inhaler with a pushing mechanism and of the construction of the system comprising a capsule (similar to the sixth or ninth embodiment) and inhaler: FIG. 9a shows a capsule element with an associated annular holder, FIG. 9b shows the tube of the inhaler in which capsule and ring are placed, FIG. 9c shows the closure of the capsule in the tube, FIG. 9d shows an exploded view of the components or groups of components of the inhaler, FIG. 9e shows the same exploded view in schematic longitudinal section, FIG. 9f shows the finished assembled system comprising capsule and inhaler in the transporting state and FIG. 9g shows the system in the state ready for use.

FIG. 10 is a schematic representation of the mode of operation of a first embodiment of an inhaler according to the invention and the construction of the associated system according to the invention comprising a capsule (similar to the eighth or ninth embodiment) and inhaler: FIG. 10a shows the insertion of a capsule element into a tube, FIG. 10b shows the filling of the capsule element with powder in schematic longitudinal section through the tube, FIG. 10c shows the closure of the capsule in the tube in schematic longitudinal section through the tube, rotated through 90° compared with FIG. 10b, FIG. 10d shows an exploded view of the components or sets of components of the inhaler, FIG. 10e shows a schematic longitudinal section through the finished assembled system comprising capsule and inhaler in the transporting state and FIG. 10f shows a schematic longitudinal section through the system comprising capsule and inhaler in the state of use.

Figure 11:
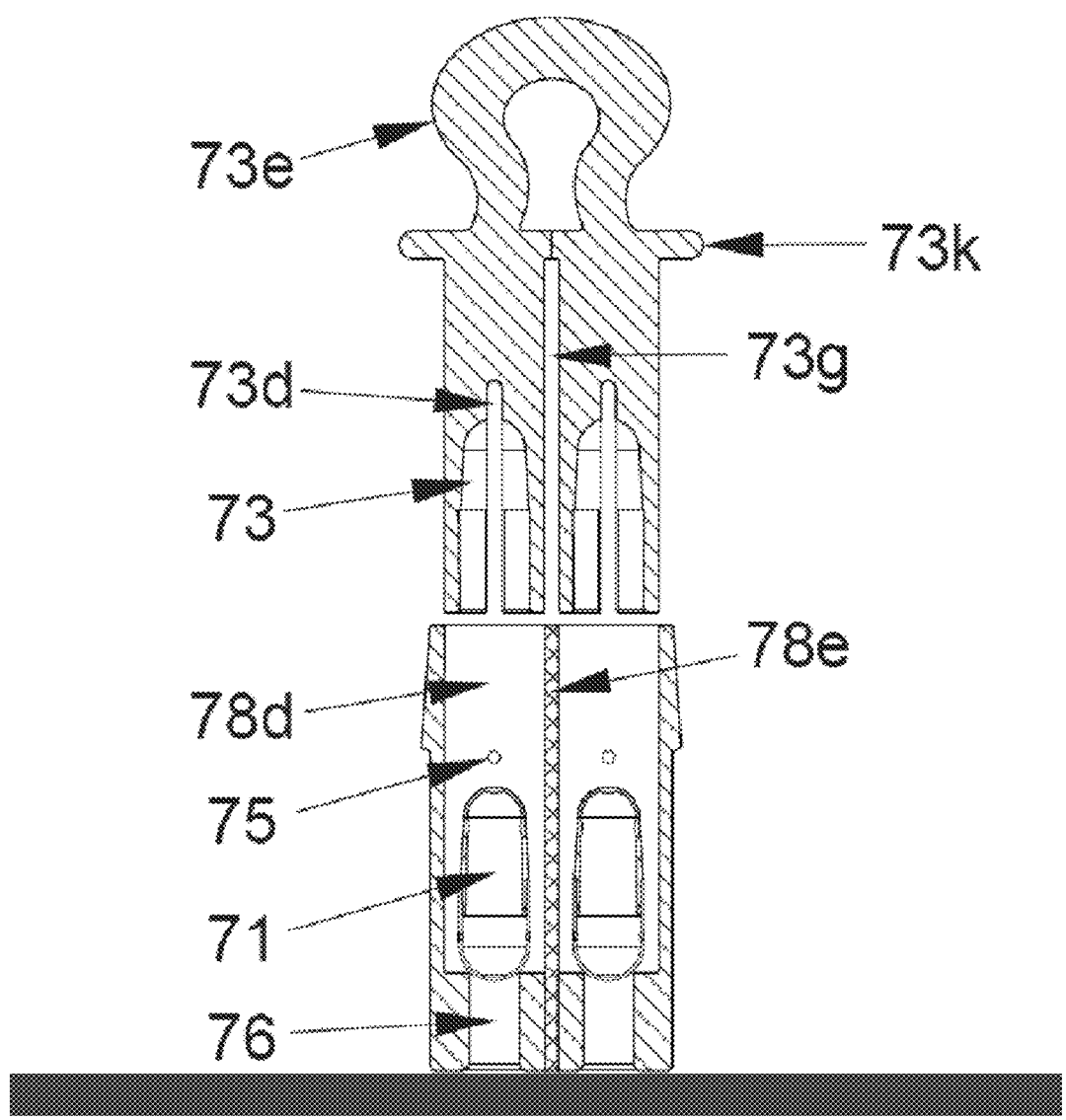

FIG. 11 is a schematic longitudinal section through a system comprising two capsules (similar to the eighth or ninth embodiment) and an inhaler according to a second embodiment according to the invention.

Figures 12A, 12B:
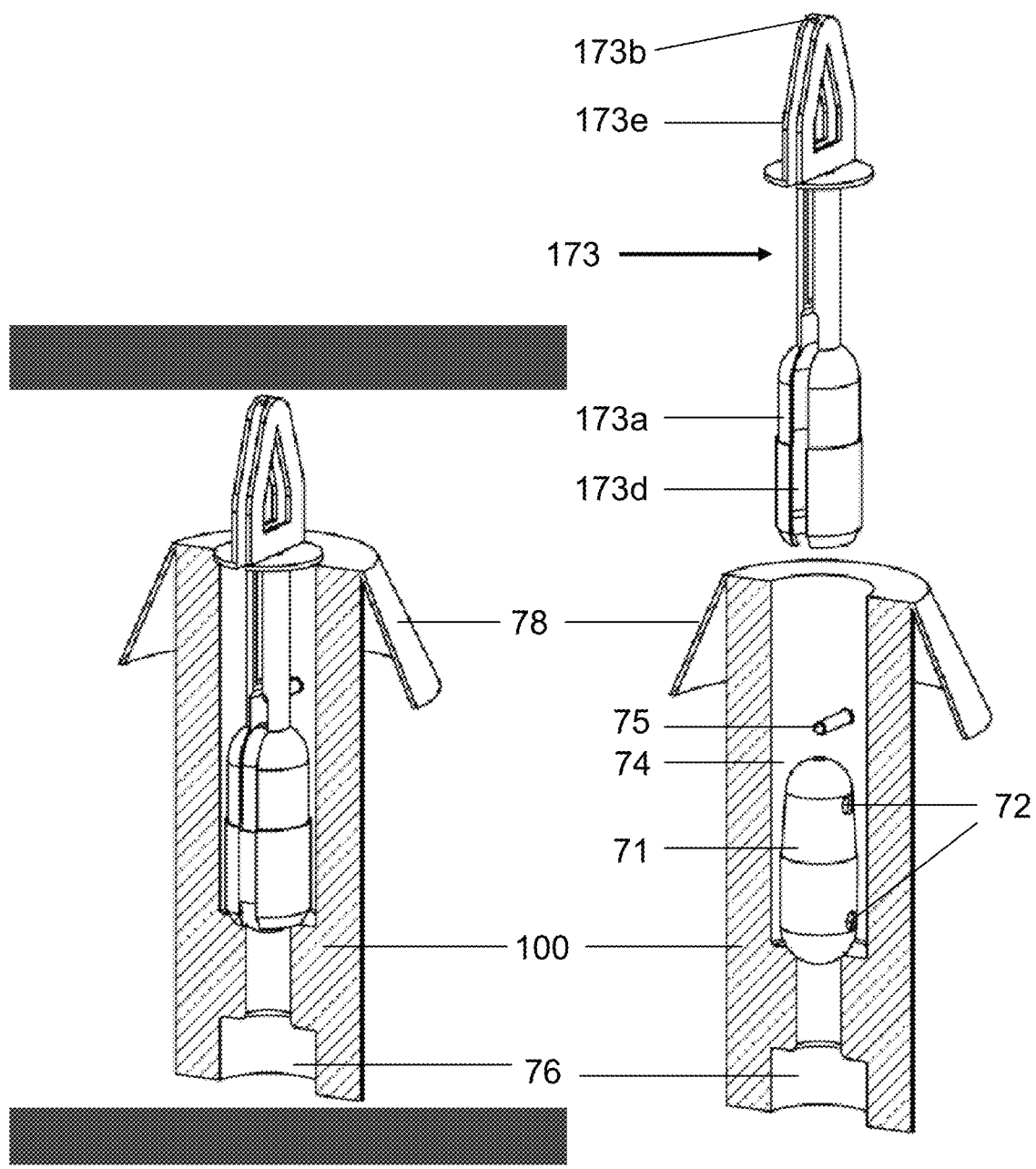

FIG. 12 is a schematic representation of a system comprising a capsule and inhaler according to a third embodiment according to the invention; FIG. 12a shows a section through the finished, assembled system composed of capsule and inhaler in the transporting state and FIG. 12b is a section through the system composed of capsule and inhaler in the state ready for use.

The embodiments of the inhalers under consideration here, which are operated with a capsule, are preferably based on the so-called Bernoulli principle: The inhalers (e.g. shown in FIG. 8c) comprise a capsule chamber (74) the length of which is adapted to the length of the capsule (71) such that the capsule (71) is able to move and vibrate in the air stream according to the Bernoulli effect. The capsule chamber (74) comprises, for this purpose, an inlet (76) for the air and an air outlet. The boundary of the capsule chamber (74) in the direction of the air outlet is preferably formed by a bar (75), screen and/or an aerodynamically advantageously shaped component which presents only minimal flow resistance. Adjoining this boundary of the capsule chamber (74) containing the air outlet is a mouthpiece (78) on which the user (not shown) inhales and thus produces the air flow needed to nebulise the capsule contents.

Various special capsules for use in inhalers operating by the Bernoulli method will be described hereinafter.

FIG. 1 schematically shows a special capsule consisting of a capsule cap (1) and capsule body (2) both of which are cup-shaped and can be fitted into one another telescopically by means of their openings. These and all the subsequent drawings are to be understood as being sketches in which wall thicknesses and similar details are not shown in full or in some cases are not necessarily shown to scale with one another.

The capsules shown in this and subsequent Figures are preferably filled with a powdered medicament preparation. Preferably, the capsule cap (1) and the capsule body (2) are in the form of a cylinder open at one end with a round cross-section and convex, virtually hemispherical at the other, closed end. The capsule cap (1) and capsule body (2) both preferably consist of polypropylene (PP) or polyethylene (PE), particularly preferably high-density polyethylene with a density of between 950 and 1000 kg/m$^3$. Alternatively embodiments are also possible in which the capsule cap (1) and capsule body (2) are made of different materials, for example the capsule body of PP or PE and the capsule cap of gelatine. The capsule sizes are matched to the respective inhalers or the dimensions of the capsule chambers contained therein in which they are to be inserted. Typical lengths of the assembled capsules are for example 9 mm to 22 mm with external diameters of 4 mm to 10 mm. Examples of the capsule dimensions can be found in the disclosure of WO2006/074982 A2 on page 6 lines 6 to 27. The contents of all the lines quoted are to be incorporated in full herein.

With regard to the material design of the capsule, for which all pharmaceutically acceptable plastics may be used, besides the preferred material polyethylene, reference is made in this respect to the disclosure in the application WO2006/074982 A2 on page 5, lines 6 to 31. The contents of these lines are hereby incorporated in full in the present application, including the features.

FIG. 1a shows the two separate capsule elements (1) and (2) with the prefabricated holes (6) and (7) before they are fitted together. In the embodiment shown here, during the telescopic fitting together, the capsule cap (1) is fitted onto the capsule body (2). (The opposite case of inserting the capsule cap (1) into the capsule body (2) is also feasible; in this case all the references to "inside" and "outside" that follow must be reversed). For the embodiment chosen here in which the capsule cap (1) is fitted onto the capsule body (2) the external diameter of the capsule cap (1) in the region of its cup opening is rather larger than the capsule body (2). The external diameter of the capsule body (2) at this point is comparable in size to the internal diameter of the capsule cap (1), while the diameters are matched to one another in terms of their tolerances such that when the capsule elements are joined together they fit into one another in the region of the capsule casing regions with no appreciable gaps. In the representation shown, after the capsule elements have been fitted together, the capsule body (2) thus forms the inner wall of the capsule in the region of the two abutting casing regions of the capsule elements. The capsule is filled with the preferably powder medicament preparation, e.g. by filling the preparation into the capsule body. After the filling, the capsule cap (1) is pushed onto the capsule body (2) up to a first insertion position. The arrow marked "p" in the Figures indicates the direction in which the capsule elements are, or have been, pushed together. It is further intended to symbolise the pressure that has to be applied for this pushing together.

In the first insertion position (cf. FIG. 1b) latching elements on the outer casing region of the capsule body (2) and latching elements on the inner casing region of the capsule cap (1) engage with one another. In all the Figures shown here, these latching elements are shown in the form of annularly encircling projections or beads and grooves or corrugations. Thus, the capsule body (2) in FIG. 1 has for example an outwardly directed encircling bead (5) which in the first insertion position engages in a first annularly encircling corrugation (4) on the inside of the capsule cap (1). The same effect would be achieved by an annular groove in the outer casing region of the capsule body (1), while in the insertion position an annularly encircling projection on the inner casing region of the capsule cap (1) engages in this groove. However, the latching elements do not necessarily have to be of annular configuration, but may also be formed by rather dot-like elevations in the capsule body and matching depressions in the capsule cap, or vice versa. In a preferred embodiment the capsule body comprises a plurality of dot-like, annularly arranged elevations which engage in a corresponding, preferably annularly encircling groove on the outside of the capsule cap. With regard to the design of a somewhat dot-like latching configuration, reference is made here to the disclosure of WO2006/074982 A2 on page 7 line 1 to page 8 line 32. The contents of all the lines quoted are hereby incorporated in full.

In the first insertion position (cf. FIG. 1b) the casing regions of the capsule body (2) and capsule cap (1) preferably overlap such that the casing of the capsule body (2) covers the hole (6) in the capsule cap (1) from the inside and the casing of the capsule cap (1) covers the hole (7) in the capsule body (2) from outside. The capsule is completely closed in this first insertion position.

In the second insertion position (cf. FIG. 1c) the capsule cap (1) and capsule body (2) are pushed so far into one another that the respective holes (6) and (7) are in registry with one another. The capsule is thus "opened" in this second insertion position, in the sense that powder can be expelled from the interior of the capsule. The prefabricated hole (6) in the casing region of the capsule cap (1) that is on the outside here is larger than the hole (7) of the inner casing region of the capsule body (2). The fact that one of the two holes is smaller than the other ensures that even if there are irregularities in fitting the capsule cap (1) and capsule body (2) into one another the hole diameter provided for the expulsion of the powder is not partially covered. The size of the inner hole (7) in this preferred case determines the overall size of the hole in the assembled capsule. In this way, there is no internal step on the hole on the inside of the capsule where powdered material might adhere during the expulsion process. For the second insertion position, similar latching elements to those provided for the first insertion position are provided on the capsule cap (1). Accordingly, in the embodiment shown in FIG. 1 the capsule cap (1) comprises a second corrugation (3) into which the bead (5) or other projecting latching element on the inner casing region of the capsule body (2) can engage. In this way the two holes (6) and (7) are maintained in registry and the capsule elements can no longer move relative to one another even if the capsule is moved. The latching elements needed for the first and second insertion positions may be formed for example by shaping during the injection moulding of the capsule cap (1) and capsule body (2) or may be produced on the components by material deformation. Thus, for example, a bead (5) running around the inside of the capsule body may be accompanied by a corrugation running around the outside.

In addition to the structuring of the capsule elements, which is to be regarded as macroscopic, another embodiment of the capsule according to the invention has a micro- or nanostructure or surface coating on the inside on a capsule element. This is, in particular, the capsule element that forms the outer wall of the capsule when the capsule casings are abutting on one another—the capsule cap (1) in the example of FIG. 1. The microstructure is preferably located on the inside on the casing surface facing the other capsule element. In particular, the microstructure extends over a in an annular region of the inner casing surface, this annular region forming a direct wall of the cavity of the capsule when the capsule is in the first insertion position (FIG. 1a), and abutting on the outer casing surface of the other capsule element (the capsule body (2) in the example shown in FIG. 1) when the capsule is in the second insertion position (FIG. 1c).

This microstructure gives rise to a so-called lotus effect, i.e. it reduces the adhesion of certain materials to this surface. To achieve the optimum effect, the nature of the microstructure must be selected such that it offers the least adhesion properties for the specific pharmaceutical preparation that is to be stored in the corresponding capsule type. As a result, no or very little material from the pharmaceutical preparation, for example powder, adheres to the inner wall of the capsule. This has the effect, particularly in the annular region described, that when the capsule is pushed together from the first to the second insertion position there is no friction caused by material adhering to the wall. Expansion of the microstructure to all the inner wall regions of the capsule is also possible and has the effect that no material is left behind in the capsule as a result of adhesion to the wall when the material is expelled during a nebulisation process. The microstructure is formed by elevations and/or depressions in the surface. The elevations and/or depressions may take the form of points, hemispheres, planar surfaces, wedges, etc. They may have a random arrangement or may be ordered, e.g. in rows, circles, zigzags, in a meandering shape, etc.

The distance between the elevations on the surface structure is in the range from 0.1 to 200 microns, preferably 0.1 to 100 microns. In the case of powdered pharmaceutical preparations, structural dimensions are preferred which are less than the particles sizes of the powder. Most preferred are heights of elevations or depths of depressions in the range from 0.1 to 50 microns and distances of from 0.1 to 10 microns.

With regard to methods of producing such a microstructure and its properties, reference is made here to the disclosure of WO2004/062716 A1 on page 11 line 1 to page 13 line 13. The contents of these lines are hereby incorporated in the present application in full, including their features.

Preferred methods of applying a microstructure to inner capsule walls are those methods that do not introduce any additional material into the capsules, i.e. those microstructures that may be formed solely in the material that constitutes the respective capsule element. In the preferred case of capsule elements produced by injection moulding, the microstructures have preferably already been reproduced in mirror symmetry in the mould inserts of the injection moulding tools, so to speak, so that the capsule elements are provided with these microstructures and also the prefabricated holes during the first manufacturing step. Alternatively microstructures of this kind may be created on the inner capsule walls by subtractive surface treatment such as etching or galvanic material removal or by subsequent embossing, for example using an expandable punch that is inserted in the main opening of the capsule element.

FIG. 2 shows a second embodiment of a capsule made up of a capsule cap (1) and a capsule body (2). This embodiment differs from the first only in that the capsule cap (1) and capsule body (2) comprise a plurality of prefabricated holes (6*a*) and (6*b*) or (7*a*) and (7*b*) respectively. In the first insertion position (not shown) all these holes are closed off by the other capsule element analogously to the first embodiment. In the second insertion position (FIG. 2*b*) the respective holes (6*a*) and (6*b*) of the capsule cap (1) are in registry with the holes (7*a*) and (7*b*) of the capsule body (2), so that the capsule is opened at a number of places. In the embodiment shown two holes (6*a*, 6*b*) or (7*a*, 7*b*) are formed in the capsule cap (1) and capsule body (2), respectively, which result in two openings in the capsule in the second insertion position. However, any desired number of holes may be provided in this way. Depending on the configuration of the casing regions of the capsule cap (1) and capsule body (2) the holes may be distributed over the circumference and length of the capsule. Particularly preferably, the resulting opened capsule comprises two holes which are located on the casing region of the capsule close to the opposite ends of the capsule, i.e. at a clear spacing from one another, based on the length of the capsule.

FIG. 3 shows a third embodiment of a capsule that may be made up of a capsule cap (1) and a capsule body (2). This embodiment differs from the first only in that the holes (6) and (7) in the capsule cap (1) and capsule body (2) have an elliptical shape instead of a circular one. The longitudinal axes of these ellipses are rotated through 90° relative to one another. This ensures that in the event of irregularities during the pushing together, the openings formed by the covering process always occupy a constant overall surface area. Instead of an elliptical hole shape, correspondingly aligned oblong holes may also be used at this point.

FIGS. 4 and 5 schematically show the capsule body (2) and capsule cap (1) in cross-section and after fitting together, for various embodiments. In order that the respective holes (6) and (7) can be brought cleanly into registry when the capsule cap (1) and capsule body (2) are fitted together the capsule elements have to be fitted into one another in alignment with respect to their circumference. This requires a structure and counter-structure similar to that of a lock and key principle at the edges or respective casing surfaces of the capsule cap (1) and capsule body (2). Moreover, it is advantageous to have a longitudinal guide which ensures that after a controlled first fitting together of the capsule elements, no unwanted rotation of the capsule elements relative to one another can occur. In the embodiment shown in FIG. 4 the capsule cap (1) and capsule body (2) are similarly configured with a slightly elliptical cross-section. The elliptical shape forces the correctly oriented fitting together of the two capsule elements. When the elliptical capsule elements are brought together there are consequently two possible orientations, rotated through 180' relative to one another. Preferably, therefore, one of the two capsule elements, particularly preferably the outer one (thus in this example the capsule cap (1)), should not only comprise the at least one prefabricated hole (6) but should also comprise a duplication of the hole structure offset through 180° along the circumference of the capsule element. Thus, independently of the orientation when two elliptical capsule elements are brought together a hole (6) is always exposed when they are pushed together into the second insertion position.

In the embodiment according to FIG. 5, the outer region of the capsule body (2) in addition to the latching elements (not shown) should have a tongue (8) extending parallel to the longitudinal axis, the contour of which fits a groove (9) that is also provided longitudinally on the inside of the capsule cap (1). The capsule elements can only be pushed together in the azimuthal alignment in which the tongue (8) and the groove (9) engage in one another. The tongue (8) and the groove (9) form a guide along the entire insertion length.

If desired, a plurality of tongue and groove pairs at different spacings from one another and/or of different widths may also be arranged on the casing surfaces of the capsule elements.

In an embodiment not shown here, the structural pair comprising the tongue (8) and groove (9) shown may also have a curved configuration as a result of which the pushing together of the capsule elements forces them to rotate relative to one another. This may be advantageous particularly for the objective of covering and exposing a plurality of holes in the capsule.

FIG. 6 schematically shows another embodiment of a capsule according to the invention consisting of a capsule cap (1), capsule body (2) and a ring (22). The capsule cap (1) and capsule body (2) are both also cup-shaped analogously to the embodiment shown in FIG. 1 and can be telescopically fitted into one another through their openings, while in this respect aspects described with reference to FIG. 1 are also valid here. For reasons of easier filling, the Example shown in FIG. 6, unlike the other examples of representations, shows an embodiment in which the capsule cape (1) is pushed into the capsule body (2). However, embodiments with a cap pushed on externally are also possible. The capsule body (2) with a larger hole (7) compared with the capsule cap (1) thus forms the outer wall of the capsule in the region of the two abutting casing regions of the capsule elements, the capsule casing regions of the two capsule elements comprise structured portions which interact with one another analogously to the previous examples.

FIG. 6a shows the two separate capsule elements (1) and (2) with the prefabricated holes (6) and (7) before they are fitted into one another and before they are joined with the ring (22).

FIG. 6b shows the capsule body (2) after joining with the ring (22). The ring (22) covers the hole (7) in the capsule body (2). This is preferably the situation in which the preferably powdered pharmaceutical preparation is transferred into the capsule body (2) which is then closed off with the capsule cap as shown in FIG. 6c. In this design, the capsule cap (1) may be pushed into the capsule body (2) directly until the final insertion position is reached.

FIG. 6c shows the assembled capsule (11) in which, analogously to the example in FIG. 1, the capsule cap (1) and capsule body (2) are latched to one another by means of latching elements (3) and (5). The prefabricated holes (6) and (7) overlap in this assembled capsule, but the resulting hole is covered by the ring (22) in this state. The capsule (11) may be stored thus or inserted in a suitable inhaler. Alternatively to the capsule (11) shown here, in this design, with the prefabricated holes (7) sealed off by means of another, for example annular, component, the capsule elements may also be configured so that after the assembly a hole (7) in the capsule body (2) does not necessarily have to be in registry with a hole (6) in the capsule cap, but in each case the capsule casing of the other capsule element in the assembled state of the capsule (11) is so short that it leaves the respective hole exposed. In this alternative embodiment (not shown) the capsule body (2) comprises a prefabricated hole (7), the capsule cap (1) has a hole (6) that fits this hole (7) and the casing of the capsule cap (1) in the assembled state of the capsule ends above the hole (7) and leaves it exposed.

FIG. 7 schematically shows another embodiment of a capsule. FIG. 7a shows the capsule as a whole with its filling. The capsule is substantially cylindrical with hemispherical upper and lower ends. The closed capsule (71) contains inside it a measured dose of the powder (40).

In FIG. 7b, holes 42a and 42b have been provided in the hemispherical upper end or cover and in the lower end or base of the capsule. For expelling the powder, particularly using the Bernoulli effect in an inhaler, at least one hole is required in the base and at least one hole in the cover of the capsule. It is also possible to use more than one hole in the base and cover. The hole sizes are preferably between 0.01 and 5 mm in diameter, preferably between 0.5 and 1.5 mm. The holes are preferably circular but may also be oval, square or of any other shape. The holes may be shaped in the injection moulding process, drilled with conventional drills or lasers, punched or formed in any other way, before the capsule is filled with powder.

In FIG. 7c the holes (72) have been placed in the parallel walls or in the cylindrical casing region of the closed capsule 71. In this way the powder can be more easily stored in the capsule with prefabricated holes as the capsule can be stored in precisely fitting manner in a cylindrical tube which then tightly seals the capsule in the casing region.

FIG. 7b and FIG. 7c simply show variants in which the holes (42a, 42b and 72) are formed either in the hemispherical regions or in the cylindrical regions of the capsule (71). In addition, however, variants of a capsule (71) with a total of at least two holes (42a, 42b and 72) are possible, in which the hole or holes (42a, 42b or 72) is or are provided on one side of the capsule (71) in the hemispherical region and the hole or holes (42a, 42b or 72) is or are located on the other side of the capsule (71) in the cylindrical casing region. The at least two holes (42a, 42b and 72) may, moreover, be arranged offset by 180° C. or other angular units, in relation to the circular circumference of the capsule (71). Also, many variations in the distribution of varying numbers of holes (42a, 42b and 72) on the capsule (71) are also possible; for example, there may be only one hole (42a, 42b or 72) on one side (the bottom, in relation to FIG. 7b) and at least two holes (42a, 42b or 72) on the other side (the top).

FIG. 8 schematically shows the mode of operation of a device (70) or inhaler in which a capsule (71) (FIG. 8a) with two prefabricated holes (72a, 72b) is stored in the device in such a way that the holes (72a, 72b) are closed off in the storage state (FIG. 8b) and the capsule (71) for using the device is pushed out of the storage state into a capsule chamber (74).

FIG. 8a shows the otherwise closed capsule (71) with prefabricated holes (72a, 72b). The capsule (71) is substantially cylindrical with hemispherical ends (71a, 71b). The holes (72a, 72b) are located in the parallel walls of the capsule or in the casing region of the capsule close to the hemispherical ends in each case. Analogously, in this context, capsules according to other embodiments may be used, particularly according to the capsule (11) shown in FIG. 7c.

FIG. 8b shows the capsule in its storage position in a device (70). In this storage position the capsule (71) is held firmly in a tube (73). This prevents powder from escaping from the capsule (71) as the inner wall of the tube covers the holes (72a, 72b). A capsule chamber (74) is formed within the device (70). The capsule chamber (74) is directly adjacent to the tube (73) and has a rather larger, preferably circular diameter than the tube (73). The capsule chamber (74) is delimited by a bar (75) or some other preferably aerodynamically shaped component in the air outlet region.

In FIG. 8c the device (70) is ready for use, i.e. it is in the state of use. The capsule (71) has been pushed through the inlet (76) into the capsule chamber (74). For this purpose, a piston shaped pusher has been inserted into the tube (73) on the side of the capsule (71) opposite the capsule chamber (74). The pushing surface of the pusher delimits the capsule chamber (74) on the side opposite the air exit, in the state of use. For use, the user breathes in through a mouthpiece (78) in the direction of the arrow (92) in the figure. Air enters the device (70) in the direction of the arrow (91) in the figure through the inlet (76), or through an air guide in the pusher which is preferably in the form of a hollow piston. In the air stream the capsule (71) vibrates in the capsule chamber (74), while the powder is expelled from the capsule (71) through the holes (72a, 72b).

In another embodiment according to the invention, not shown, the capsule is already stored in the vibration chamber or capsule chamber (74) and the capsule (71) is enveloped in a preferably tubular film. The film fits closely against the cylindrical casing region of the capsule (71) and closes off the holes (72). Preferably, the materials of the film and capsule wall may be selected so that the preferably elastic and/or easily flexible film fits tightly against the capsule wall by electrostatic attraction. At one end point the capsule (71) is preferably not fixedly enclosed by the film and at the other end it projects significantly beyond the capsule (71) and/or is connected to a pull strip. This film portion projecting at the end of the capsule and/or the pull strip is located in the air inlet, in the transporting state of the inhaler, such that at this point part of the film and/or of a pull strip protrudes from the inhaler. Before the inhaler is used the film is pulled off by means of this protruding part and/or this pull strip through the air inlet of the capsule which does not fit through the air inlet. For example, in the air inlet, there is a bar (75) or another obstacle which stops the capsule (71) (in this example, the film or the film tube rests only on one side of the strip in the air channel). If the film or the film tube is pulled away but the capsule is retained, the capsule slides out of the preferably flexible film or film tube. As a result the holes (72) are exposed, the capsule (71) is given full room to manoeuvre in the capsule chamber (74) and the inhaler is ready for use.

Alternatively, the protruding part of the film or the pull strip may also be located in the mouth piece of the inhaler and may be pulled out of the system through the mouth tube. Generally, the opening through which the film is pulled out of the system may also be closed off in the transporting state. In the embodiment in which the protruding film portion or the pull strip is located in the mouth tube, the mouth tube may for example be closed off by a cap fitted to the mouthpiece (78) which has to be removed before the film can be pulled out. A cap of this kind may also be directly connected to the pull strip or the film.

FIG. 9 schematically shows the construction of another embodiment of a system comprising an inhaler and capsule, the mode of operation of the system being similar to that shown in FIG. 8. The partial images 9a to 9f at the same time schematically show the sequence of the assembly of the system. First of all (FIG. 9a) a capsule body (2) with at least one prefabricated hole is inserted in a ring (22) which exactly surrounds the capsule body (2) in the region of its at least one prefabricated hole and thus seals the hole. Optionally, the ring (22) comprises on the inside one or preferably more small projections which, when the capsule body (2) and ring (22) are joined together define a lower position of the capsule body (2) in the ring (22), so that the capsule body (2) cannot move downwards within the ring and/or a fit is formed between the capsule body (2) and ring (22) by means of which the capsule body (2) is retained in the ring (22). Features from this embodiment relating to the ring (22) may be transferred analogously to the ring (2) from the embodiment according to FIG. 6. FIG. 9b shows how the capsule body (2) in the ring (22) is inserted in a tube (73) from below. The tube (73) in this embodiment forms the capsule receptacle. Preferably, the ring (22) latches from inside with the tube (73) in a first latching position, e.g. in which an encircling bead (22a) or other type of latching element engages from inside the tube (73) in a corresponding recess. The tube (73) is open at its upper end so that the capsule body (2), the opening of which faces upwards when inserted in the tube (73), can be filled with powder (40) from above through the upper opening of the tube (73). FIG. 9c then shows how, after being filled with powder (40) (not shown), the capsule cap (1), which preferably also comprises at least one prefabricated hole, is inserted in the tube (73) from above and thus inside the tube (73) closes off the capsule body (2), or the capsule (71) is assembled in the tube (73). The tube (73) meanwhile surrounds the capsule cap (1) in precisely fitting manner, preferably with an upper collar (73a) so that the at least one hole (72b) in the capsule cap (1) is covered or sealed by the tube (73).

FIG. 9d and FIG. 9e show how the other components of the inhaler—mouthpiece (78) and pusher (77)—are assembled with the unit consisting of the tube (73), powder-filled capsule (71) and ring (22); the mouthpiece (78), which is preferably formed in one piece, contains the capsule chamber (74) and a bar (75) as a boundary at the top inside the capsule chamber (74). The mouthpiece is placed on the tube (73) from above, thereby latching with the tube (73). For this purpose, latching elements alternating with one another are formed on the mouthpiece (78) and tube (73), e.g. in the form of an annular bead (78b) mounted at the bottom inside the mouthpiece, this bead engaging in an equally annular corrugation (73b) on the outside, at the top of the tube (73). On the opposite side to the mouthpiece, i.e. from the bottom, in the figure, a pusher (77) is inserted in the tube (73). The pusher (77) contains an inlet (76) through which air can flow into the capsule chamber (74) later during use of the inhaler. Preferably, the pusher at (77) is embodied as a hollow piston and/or the inlet (76) is formed by a radially symmetrical passage along the main axis of the pusher (77). The pusher (77) comprises a tapered portion (77a) at its upper end, which is of such dimensions that it is able to penetrate into the ring (22).

FIG. 9f shows, in schematic longitudinal section, the finished assembled system comprising the capsule (71) and inhaler in the transporting state: the capsule (71) has been pre-installed in the inhaler so that its prefabricated holes (72a), (72b) are covered or sealed off by the ring (22) and/or by the inside of the tube (73) (in the embodiment shown, having a total of two prefabricated holes (72a), (72b), one hole (72a) is sealed off by the ring (22) and one hole (72b) is sealed off by the inside of the tube). The pusher (77) projects with its lower end out of the inhaler. In order to activate the inhaler, i.e. to change the device form the transporting state to usage state, the pusher is pressed into the device at its end protruding from the bottom of the device. Preferably the lower end of the pusher (77) is broadened for this purpose so that when it is pressed with the hand it fits comfortably against the ball of the user's or patient's thumb. As it slides in, the pusher (77) preferably abuts with an annularly shaped contact surface against the capsule (71) from below and pushes the latter—as a result of it being held in the ring 22—initially together with the ring (22) further in the direction of the capsule chamber (74), until the ring (22) latches in a second latching position. As the pusher (77) is pushed further into the tube (73) the pusher (77) enters the ring (22) and with its tapered portion (77a) pushes the capsule (71) out of its close-fitting holder in the ring (22) into the capsule chamber (74). The tapered portion (77a) is preferably designed to be such a length that the tapered region of the pusher (77) can be pushed through the ring (22) and through the collar (73a) of the tube (73) until the upper edge of the pusher (77) forms the lower boundary of the capsule chamber (74). Preferably, in the pushed-in state (usage state of the inhaler, cf. FIG. 9g) the upper edge of the pusher (77) lies flush against the upper edge of the tube (73). The gap which is formed in the base of the capsule chamber (74) between the upper edge of the pusher (77) and the collar (73a) at the top of the tube (73) depending on the design of the system—e.g. as a result of a capsule cap (1) which is larger in diameter than the capsule body (2) and tapered portion (77a)—is preferably sealed by the ring (22) to prevent the ingress of secondary air. For this purpose the ring (22) consists of an at least partially elastic material and in this pushed-in state (cf. FIG. 9g) of the pusher (77) it seals off the pusher (77) against the tube (73) underneath the collar (73a).

The inhaler is then ready for use, as shown in FIG. 9g: The holes (72a), (72b) are exposed and the capsule (71) has room for manoeuvre in the capsule chamber (74), as required for the vibratory movement according to the Bernoulli effect. Preferably, at least one and preferably two spring arms (77b) are formed on the side of the pusher (77), which engage in corresponding recesses (73f) on the inside of the tube (73) in the pushed-in state. By their engagement inside the tube these spring arms (77b) prevent the pusher (77) from being pulled out of the device. It is thus made clear to the user that this is a device for one-time use.

FIG. 10 schematically shows the construction of another embodiment of a system comprising an inhaler and a powder-filed capsule (71), in which, in particular, a capsule according to the embodiments shown in FIG. 7c or FIG. 8 can be used. The partial images 10a to 10e at the same time schematically show the sequence of assembly of the system.

First of all (FIG. 10a) a capsule body (2) with at least one prefabricated hole is inserted from above in a tube (73) which in this embodiment is essentially open only at one end, forming the capsule receptacle. The tube (73) surrounds the capsule body (2) in the region of its at least one prefabricated hole in closely fitting manner and thereby seals off the hole in the capsule body (2). The opening at one end of the capsule body (2) meanwhile faces upwards, i.e. in the direction from which the capsule body (2) has been inserted in the tube (73). Depending on the configuration of the capsule receptacle it is advantageous to insert the capsule (71) into it in correctly oriented manner. In the embodiment shown here the capsule receptacle comprises for example two longitudinally extending slots (73d) the function of which will be explained in more detail by means of the description of FIG. 10f. To ensure that the holes (72a, 72b) are sealed off by the insertion of the capsule (71) in the capsule receptacle, the capsule (71) is preferably inserted in the tube (73) in oriented manner such that the holes (72a, 72b) are not located in the region of the slots (73d). To predefine the orientation of the capsule (71) as it is inserted in the capsule receptacle, the technique described with reference to FIGS. 4 and 5 may be used. Thus, the capsule (71) and the interior of the capsule receptacle may, for example, be slightly elliptical in configuration in their short diameter. Alternatively, capsules (71) or the interior of the capsule receptacle may comprise corresponding pairs of longitudinally extending tongues and grooves: for example a longitudinal groove or longitudinal channel on the outer wall of the capsule (71) in conjunction with a longitudinally extending tongue inside the capsule receptacle.

FIG. 10b shows the filling of the capsule body (2) inside the tube (73) with powder (40) which is introduced into the opening at one end of the capsule body (2) from above. Then (FIG. 10c) the capsule cap (1) is introduced into the tube (73) from the same direction, i.e. from above, in the drawing, so that the capsule (71) is closed off inside the tube (73). FIG. 10d shows how the other components of the inhaler—mouthpiece (78) and bar (75)—are assembled with the unit consisting of the tube (73) and powder filled capsule (71): the tube (73) is inserted from above (now shown in FIG. 10d, upside down compared with FIG. 10c) through an opening in the mouthpiece (78), preferably up to a lower stop formed by the capsule chamber (74). The end from which the tube (73) is inserted is the mouth end of the mouthpiece, i.e. the end where the patient using the inhaler places their lips. After the insertion of the tube (73) in the mouthpiece (78), a bar (75) is pushed in through a guide provided laterally on the mouthpiece. The bar (75) subsequently forms the upper boundary of the capsule chamber (74) located in the mouthpiece (78). Before the insertion of the bar (75) the tube (73) has been inserted in the mouthpiece oriented so that two slots (73d) provided on the tube abut on the mouthpiece (78) inside the passage and thus allow room for the insertion of the rod (73). In this way the bar (75) can be introduced into the mouthpiece (78) so that, without being impeded by the tube (73), it penetrates through the mouthpiece (78) preferably transversely through the main axis of the device from one outer wall to the other. The oriented insertion of the tube (73) into the mouthpiece (78) is preferably predetermined by the external shape of both components. Thus, the embodiment shown comprises, for example, a mouthpiece (78) with an essentially oval or trapezoidal cross-section from the mouth end of the mouthpiece (78). The tube (73) is formed in its upper region—remote from the capsule receptacle—preferably in the form of a cap which completely covers the mouthpiece at its end destined for the mouth. This cap structure of the tube (73) forms the counterpart to the substantially oval or trapezoidal shape of the mouth end of the mouth piece (78), so as to provide orientation during insertion, as the result of the oval shape or the preferential axis of a non-circular symmetry. The cap structure of the tube (73) shown in FIG. 10 also has the additional advantage that at the mouth end the outer surfaces of the mouthpiece (78) in the regions where the patient places his lips, are covered by the tube (73) in the transporting state. Thus, even if the device is removed from its outer packaging much too early, it is ensured that the regions for lip contact remain free from contamination until the device is used.

The bar (75) forms the upper boundary of the capsule chamber (74) inside the mouthpiece (78). Apart from the bar (75), all the other components of the capsule chamber (74) are formed in one piece by the mouthpiece (78). At the lower end of the capsule chamber (74), i.e. at its end opposite the bar (75) and the mouthpiece opening, the mouthpiece comprises an inlet (76) which, in the embodiment shown, is formed as a central passage along the main axis of the system.

The inhaler shown here preferably consists of only three parts—mouthpiece (78), tube (73) and bar (75), all of which can be cheaply manufactured by plastics extrusion, so that an inhaler of this design is highly suitable for single use, i.e. as a disposable item to be discarded after one use.

FIG. 10e shows the system of inhaler and capsule (71) in the assembled state which in this case also corresponds to the transporting state. The prefabricated holes (72a, 72b) (not shown) in the capsule (71) are closed off by the inner wall of the tube (73). For capsules (71) wherein one capsule element, e.g. the capsule cap (1), has a larger external diameter than the accessible part of the other capsule element, e.g. the capsule body (2), the tube (73) has a corresponding variation in the internal diameter: the capsule element with the smaller diameter is located further inside the tube (73) than the capsule element with the larger diameter, and the internal diameter of the tube (73) is adapted to the external configuration of the capsule (71) accordingly, so that it also becomes broader stepwise from the inside to the outside. Thus in the transporting state the capsule (71) is enclosed in the system with no appreciable room for movement. For secure fitting of the tube (73) in the form of a cap on the mouthpiece (78), the tube preferably comprises in its upper region spring arms (73f) which press against the inner wall of the mouth tube (78d) from inside, in the transporting state, which forms the air outlet from the capsule chamber (74) at the mouth end of the mouthpiece (78). Preferably the mouth tube (78d) and the capsule chamber (74) have the same diameter.

In order to use the inhaler the tube (73) is pulled out of the mouthpiece (78), as shown in FIG. 10f. The slots (73d) in the tube (73) enable the tube (73) to be pulled past the bar (75). The bar (75) inserted in the mouthpiece (78) and extending transversely through the mouthpiece opening ensures that the capsule (71) remains in the capsule chamber (74) in the mouthpiece (78) and cannot be pulled out again with the tube (73). If the tube (73) is pulled out of the mouthpiece (78), the spring arms (73f) which have previously been compressed in the mouth tube (78d) preferably spread out in an outward direction such that the tube (73) cannot be reinserted in the mouthpiece (78) without destroying it (without auxiliary means). In this way the user is shown that the device is a disposable item or one way product. To make it easier for the user to pull the tube (73) of the out of mouthpiece (78), the tube (73) preferably comprises a gripping aid (73e). This gripping aid may for example be formed, as shown in FIG. 10d, by rifling on the outer lateral surface in the cap region of the tube (73) or (not shown) by a strap. This strap is preferably located centrally at the top of the cap region of the tube (73), i.e. at the opposite end to the insertion opening for the capsule (71), and contains an opening which is of such a size as to allow the user to place a finger (preferably the index finger) in the opening in order to pull the tube (73) out of the mouthpiece (78). To enable the mouthpiece to be held comfortably with the fingers of the other hand at the same time, it is preferably provided with a gripping surface (78c) which, at the moment of sliding the tube (73) out, presents the mouthpiece (78) from slipping in the hand or between the fingers. This gripping surface (78c) is preferably formed by a plurality of rounded elevations or bumps which are located in particular in the centre on the outside of two sides of the mouthpiece (78) underneath the preferably widened region for the placement of the lips.

FIG. 11 shows a system comprising an inhaler and two capsules (71). The functions in this embodiment correspond to those of the embodiment of FIG. 10, except that two capsules (71) are provided in individual capsule chambers (74). All features interacting with the capsules (71) are thus duplicated: the inhaler comprises two capsule chambers (74) with two inlets (76), to rods (75) and to tubes (73) with slots (73d). In the transporting state the walls of the tubes (73) enclose the capsule (71) such that the prefabricated holes (72) in the capsules are closed off. The two tubes (73) in the embodiment shown are preferably connected in a terminal region (73k) so as to be part of a cap which closes off the opening of the mouthpiece (78) in the transporting state, analogously to the embodiment in FIG. 10. A gripping aid (73e) is formed on this cap, which in FIG. 11 is shown as a strap with an opening. Before the inhalation, the user pulls the cap away from the mouthpiece (78) using the strap and thus arrives at the state shown in FIG. 11. The holes (72) on the capsule (71) are then opened after the tubes (73) have been removed from the capsule chambers (74) and the capsules (71) have the movement required for the desired vibration. The flow channels through the two capsule chambers are preferably not connected to one another. The inhaler thus comprises two mouth tubes (78d) which are separated from one another by a central wall (78e). The mouth tubes (78d) run parallel and open side by side in a preferably externally oval mouthpiece (78). The two tubes (73) are inserted in closely fitting manner in the two mouth tubes (78d) in the transporting state of the device, while a spacing (73g) is provided between the tubes to allow room for the central wall (78e).

Depending on the intended use of the inhaler the two capsules (71) may be identical or different in terms of their filling and/or external configuration. The use of a device with two identical capsules (71) has the advantage that double the formulation dose can be delivered with a single disposable device, thus saving the cost of disposable materials. The use of a device in which two capsules (71) with different fillings are stored is suitable particularly for use in therapies in which two active substances are administered simultaneously which, in some cases, cannot be stored in stable manner in a single formulation. A device of this kind ensures that the two active substances are taken in the correct proportion with one another. This rules out the possibility, for example, of a user taking the same preparation twice instead of taking two different preparations in one dosage cycle.

The capsules (71) and their associated capsule chambers (74), mouth tubes (78d) and tubes (73) may be adapted to the active substance or formulation dose for this purpose, for example they may be of different sizes or have different diameters and/or lengths.

FIG. 12 schematically shows in sectional view the construction of another embodiment according to the invention of a system consisting of an inhaler and a powder-filled capsule (71), in which, in particular, a capsule according to the embodiments shown in FIGS. 1-5, 7c or FIG. 8a can be used.

FIG. 12a shows the system composed of inhaler and capsule (71) in the assembled state, which also corresponds to the transportable state in this case. The prefabricated holes (72a, 72b) (not shown) in the capsule (71) are closed off by the inner wall of a capsule receptacle (173a) of cup-shaped configuration. The capsule receptacle (173a) is part of a pulling element (173). For capsules (71) wherein one capsule element, e.g. the capsule cap (1), has a larger external diameter than the accessible part of the other capsule element, e.g. the capsule body (2), the capsule receptacle (173a) preferably has a corresponding change in the internal diameter: the capsule element with the smaller diameter is optionally located on the capsule receptacle, as shown in FIG. 12, further along in the direction of pulling of the pulling element (173) than the capsule element with the larger diameter. The internal diameter of the capsule receptacle (173a) is adapted to the external configuration of the capsule (71), so that it also widens step by step in the same way as the capsule (71). In the transportable state the capsule (71) is thus enclosed in the system with no appreciable room for movement.

Preferably, the pulling element (173) consists of a partly flexible and/or formable material, particularly preferably a blister film which has been structured in a thermoforming process.

Preferably the pulling element (173) (as shown in FIG. 12) consists of two halves which are preferably already connected to one another by a hinge-like section such as a film hinge (173b) (i.e. the two halves are preferably manufactured as one component or produced in the same operating steps). Preferably, also, the pulling element (173) consists of a thermoformed part and/or is produced in a thermoforming process from a thermoformed film or blister film, under the effect of heat, i.e. from a film of the kind generally used in medical technology for blister packs for tablets, for example. These blister films preferably consist of a number of layers and preferably contain polyethylene and/or aluminium. Particularly preferably, films with thicknesses of less than 1 millimetre, particularly preferably with thicknesses in the range from 50 to 200 microns, such as 60, 80 or 120 microns, for example, are used. The two halves are preferably joined in a sealing process at the pulling end of the pulling element (173), in a region between the film hinge (173b) and the capsule receptacle (173a). This results in a suitable rigidity of the pulling element (173) and its gripping aid (173e). For a joint of this kind the blister film used is preferably coated with a layer of adhesive or a sealing lacquer. In the immediate vicinity of the capsule receptacle (173a) the halves are not joined together, so as to leave a slot (173d) which opens towards the capsule end of the pulling element (173). This slot (173d) extends beyond the capsule receptacle (173a) towards the middles of the pulling element (173), so as to leave a cavity into which a bar (75) of the inhaler can protrude. Preferably, the pulling element (173) in the region of the capsule receptacle (173a) is designed so that in this area the halves are arranged in self-closing manner, so to speak, i.e. the halves clamp the capsule and hold it securely in position and to some extent under spring tension. Thanks to the associated springy elasticity, the halves bend away from one another when pressure is applied to the capsule (71) along the longitudinal axis of the pulling element (173) and release the capsule (71).

In the assembly process, a pre-perforated and filled capsule (71) may be placed in one half of the capsule receptacle (173a), after which the pulling element (173) is folded up and the second half of the capsule receptacle (173a) also covers the capsule (71). After the folding operation, a slot (173d) remains on the pulling element (which is closed off by sealing, particularly in the region of the gripping aid (173e), as described hereinbefore). The capsule (71) should therefore be inserted in oriented manner in the capsule receptacle (173a), so that the holes (72) are actually totally covered by the shells of the capsule receptacle (173a). Preferably, prefabricated holes (72) are located on the capsule (71) only along a longitudinal side of the capsule (71) (or distributed over the periphery of the capsule (71) over less than 180 degrees). As a result, when placed in oriented manner in the first half of the capsule receptacle (173a)—namely, in an orientation such that the holes (72) point upwards, in relation to gravity, and preferably into the second half of the capsule receptacle (173a)—the pre-filled capsule (71) can be installed without any loss of powder through the holes.

A filling operation occurring earlier in the process may proceed as follows: The capsule (71) is filled in a positively locking capsule carrier in a filling apparatus, the capsule carrier initially receiving the capsule body (2). This capsule carrier holds the capsule body (2) during the filling process and closes off the holes (72) in the capsule body (2) during filling. After the capsule (71) has been sealed by pushing the capsule cap (1) on, the capsule carrier is rotated through 90° (with the holes pointing upwards, i.e. in the opposite direction to gravity) and the capsule (71) is pushed into the pulling element (173) by the capsule carrier or is alternatively placed in the still open pulling element, which is then folded shut and then closed or sealed. Optionally, the closure of the holes (72) in the capsule (71) by the shells of the capsule receptacle (173a) is improved by a pressing step.

As an alternative to the placing of the filled, pre-perforated capsule (71) into one half of the capsule receptacle (173a), if the material of the pulling element (173) has the requisite flexibility, it is also possible to use a process analogous to FIG. 10 for filling and inserting a pre-perforated capsule (71): the two halves of the pulling element (173) are folded shut and bent open or flipped open in the region of the capsule receptacle (or the pulling element is only bent open in the region of the capsule receptacle (173a) and then folded shut), so that a capsule element can be inserted and filled therein. Then the second capsule element is pushed onto the first and the capsule receptacles are bent back again.

Alternatively, the capsule (71) may be filled in a positively locking capsule carrier in a filling apparatus. This capsule carrier closes the holes in the capsule body (2) during filling. After the capsule (71) has been closed off by the capsule cap (2), the capsule (71) can then be pushed directly into the pulling element (173) located perpendicularly above it (from below, so to speak, in relation to the direction of gravity).

Yet another alternative method comprises using a capsule (1) with two different insertion positions, as described for example by reference to FIGS. 1 to 5. Here, a capsule element is filled and is fitted onto the other capsule element such that the holes (6, 7) of the two capsule elements are not superimposed and therefore the capsule (1) is completely closed (first insertion position). The capsule (1) is placed for example in one half of the capsule receptacle (173a), and as the pulling element (173) is folded together it is covered by the second half of the capsule receptacle (173a). Then pressure is applied to the capsule receptacle (173) from one side, for example from outside on both sides, so that on the inner capsule (1) the two capsule elements slide further into one another and the holes (6, 7) on the two capsule elements move into registry (the second insertion position is reached). At the same time, the capsule receptacle (173a) is deformed so that it fits closely against the now shorter capsule (1).

Preferably, the body (100) of the inhaler (the capsule chamber (74) being formed by the body (100)) consists of two halves, particularly preferably two thermoformed parts which divide the body (100) into two halves along a longitudinal axis (for example, FIG. 12a instead of being a schematic longitudinal section may also be interpreted as showing a thermoformed part forming the body (100) in which the pulling element (173) with capsule (71) is placed; the thin thermoformed part itself is bent round, in the plane of the drawing, to form a bead which serves as a connecting surface). Preferably, the two halves are formed from films, particularly thermoformed films or blister films, as preferably used in the pulling element (173) as described above. Thus, the pulling element (173) and body (100) may be produced from the same material.

Moreover, the body (100) preferably also comprises the region of the mouthpiece (78) on which the user's lips are placed; this lip region of the mouthpiece (78) may, however, also be formed by an additional component which is connected to the body (100).

In the assembly process, the pulling element (173) with capsule (71) is then, for example, placed in a half of the body (100) formed by a thermoformed part, for example, so that the capsule receptacle (173*a*) with the capsule (71) is located in the capsule chamber (74) and the bar (75) between the gripping aid (173*e*) and the capsule receptacle (173*a*) protrudes into the slot (173*d*) on the pulling element. Then the second half of the body (100), i.e. the second thermoformed part, for example, is placed and/or fitted onto the first half (preferably in mirror symmetry). To ensure that the two halves are joined together with no gap between the halves, the halves or the two thermoformed parts are joined together, for example by welding, gluing, laminating or preferably by joining in a sealing process. Sealing may be done using a sealing process conventionally used in the manufacture of blisters. One possible manufacturing process may comprise, for example, the application of an active sealing layer (sealing lacquer) to the halves of the body (100) directly after the thermoforming process. Sealing by pressure and heat is then only carried out later when the parts are assembled.

When thermoformed parts are used as halves of the body (100), the halves may for example be moulded from a thermoformed film which is shaped as a bead in the region of the junction, so that a support surface for the sealing or welding, etc., is retained at the otherwise thin-walled components. Alternatively, the two halves may also be manufactured as thicker-walled parts without a bead in a plastics extrusion process and welded to one another later, preferably in an ultrasound welding process.

To use the inhaler, the capsule receptacle (173*a*) is then pulled out of the mouthpiece (78). The slots (173*d*) on the capsule receptacle (173*a*) and pulling element (173) as a whole make it possible to pull the capsule receptacle (173*a*) out past the bar (75) (analogously to the function of the slot (73*d*) in FIG. 10). The bar (75) inserted in the mouthpiece (78) and extending transversely through the mouthpiece opening has the effect that the capsule (71) in the capsule chamber (74) remains in the mouthpiece (78) and cannot be pulled out with the capsule receptacle (173*a*). In an embodiment in which the body (100) of the inhaler is made up of two halves, the bar is also preferably divided into two parts such that half of the bar (75) is formed by half of the body (100). Thus, the bar (75) is an integral constituent of the body (100) and is preferably not an individual part, so that there is no need for the bar (75) to be installed additionally. When the two halves of the body (100) are welded or sealed, the two halves of the bar (75) are preferably also joined together.

To assist the user with pulling the pulling element (173) with the capsule receptacle (173*a*) out of the mouthpiece (78), the pulling element (173) preferably comprises a gripping aid (173*e*). This gripping aid (173*e*) may, for example, be formed, as shown in FIG. 12*b*, by a flat tab, preferably with an opening or gripping hole. This tab is preferably located in the centre on top of the pulling element (173) and in the assembled state of the system (FIG. 12*a*) it projects from the inhaler at the mouthpiece (78) end, so that to activate the system the user has only to pull the pulling element (173) out of the mouthpiece (78) by the gripping aid (173*e*) or tab.

Preferably, the systems described here are operated with a medicinal formulation which contains an ingredient specified in the disclosure of the European Patent Application with application Ser. No. 12/151,105.9 on page 26 line 12 to page 63 line 2, or which corresponds to one of the formulations mentioned therein. The contents of these lines are hereby incorporated in their entirety in the present application, including the features therein.

LIST OF REFERENCE NUMERALS 1 capsule cap
2 capsule body
3 corrugation (on capsule cap)
4 corrugation (on capsule cap)
5 bead (on capsule body)
6, 6*a*, 6*b* hole (on capsule cap)
7, 7*a*, 7*b* hole (on capsule body)
8 tongue (on capsule body)
9 groove (on capsule cap)
10 assembled capsule (suitable for covering hole with ring)
22 ring
22*a* bead (on the ring)
40 powder
42*a* hole (laterally at the bottom of the closed capsule)
42*b* hole (laterally at the top of the closed capsule)
70 device
71 capsule (closed)
71*a,b* hemispherical ends (of the closed capsule)
72, 72*a*, 72*b* prefabricated holes
73 tube
73*a* collar (on tube)
73*b* corrugation (on the outside of the collar of the tube)
73*d* slot (on the tube)
73*e* gripping aid (on the tube)
73*f* spring arm (on the tube)
73*g* spacing (between tubes)
73*k* terminal region
73*s* recess (in wall of tube)
74 capsule chamber
75 bar
76 inlet
77 pusher
77*a* tapered portion (on the pusher)
77*b* spring arm (on the pusher)
78 mouthpiece
78*b* bead (on the lower inner edge of the mouthpiece)
78*c* gripping surface (on the mouthpiece)
78*d* mouth tube (in the mouthpiece)
78*e* centre wall (in the mouthpiece)
91 arrow (in the direction of flow of air at the inlet)
92 arrow (in the direction of breathing in)
100 body (of the inhaler)
173 pulling element
173*a* capsule receptacle
173*b* film hinge
173*d* slot (pulling element)
173*e* gripping aid (on the pulling element)

The invention claimed is:
1. System comprising an inhaler and a capsule for use as a reservoir for a pharmaceuticals wherein the capsule comprises two capsule elements open at one end, the two capsule elements including a capsule body (2) and a capsule cap (1), which are fitted into one another telescopically through their respective openings so as to form a cavity, the inhaler comprises a capsule chamber (74), the capsule body (2) and/or the capsule cap (1) each comprise, in addition to the respective opening at one end, at least one prefabricated hole (7, 6), before the inhaler is used, the capsule (71) is stored in a capsule receptacle (173*a*), the capsule receptacle (173*a*)

sealing off at least one hole (72a, 72b) which leads into the cavity of the capsule (71), the capsule receptacle (173a) is at least partly arranged in the capsule chamber (74), and the capsule receptacle (173a) is removed from the capsule chamber (74) by means of a pulling mechanism, such that when the capsule receptacle (173a) is removed, the capsule (71) remains in the capsule chamber (74), the inhaler comprises a mouthpiece (78) with a mouth tube (78d) that connects the capsule chamber (74) to an air outlet, a component that forms or encompasses the capsule receptacle (173a) extends through the mouth tube (78d) in the inhaler, the inhaler comprises a tongue, pin or bar (75) that delimits the capsule chamber (74) and extends through the capsule receptacle (173a), and the capsule receptacle (173a) comprises a recess through which the tongue, pin or bar (75) slides during relative movement between the component and the capsule chamber (74).

2. The system according to claim 1, wherein the capsule receptacle (173a) is part of, or is formed by, a pulling element (173).

3. The system according to claim 1, wherein each of the capsule body (2) and the capsule cap (1) are of cup-shaped configuration, comprise a capsule casing which forms a cylindrically or elliptically encircling wall, and the at least one prefabricated hole (7, 6) in the capsule body (2) and/or the capsule cap (1) are arranged in an encircling wall region of the capsule casing.

4. The system according to claim 3, wherein the capsule casing of the capsule body (2) and the capsule cap (1) comprise, on sides that abut on one another in an inserted state, a structuring that enables the two capsule elements to be fitted into one another only in a defined alignment.

5. The system according to claim 3, wherein the at least one prefabricated hole (7, 6) of the capsule body (2) and the capsule cap (1) comprise two holes (7a, 7b, 6a, 6b) in upper and lower regions of the capsule casing, so that in the second insertion position the capsule (71) comprises two holes in the capsule casing.

6. The system according to claim 5, wherein each of the two holes in the capsule casing is close to a capsule end.

7. The system according to claim 1, wherein: both the capsule cap (1) and the capsule body (2) each comprise the at least one prefabricated hole (6, 7) in addition to the opening at one end, and there is an insertion position with respect to the telescopic fitting together of the capsule body (2) and capsule cap (1) in which the at least one prefabricated hole (7, 6) in the capsule body (2) and the capsule cap (1) are in registry with one another, such that the otherwise closed capsule comprises at least one hole at corresponding locations.

8. The system according to claim 7, wherein the closed capsule comprises two holes at the corresponding locations.

9. The system according to claim 1, wherein: both the capsule cap (1) and the capsule body (2) each comprise the at least one prefabricated hole (6, 7) in addition to the opening at one end, the capsule comprises, with respect to the telescopic fitting, together of the capsule body (2) and the capsule cap (1), two insertion positions, in a first insertion position, the capsule body (2) and the capsule cap (1) are fitted into one another such that the at least one prefabricated hole (7, 6) in the capsule body (2) and the capsule cap (1) are covered, and thus the cavity in the capsule (71) is closed off, and in a second insertion position, the capsule body (2) and the capsule cap (1) are fitted into one another such that the at least one prefabricated hole (7, 6) in the capsule body (2) and the capsule cap (1) overlap one another, such that the entire capsule (71) comprises a hole at a corresponding location.

10. The system according to claim 9, wherein the capsule body (2) and the capsule cap (1) comprise latching elements interacting with one another which have the effect that the two capsule elements after being fitted into one another up to the first insertion position can no longer be separated from one another non-destructively and/or in that the relative position of the two capsule elements relative to one another is fixed.

11. The system according to claim 9, wherein the capsule body (2) and the capsule cap (1) each comprise the at least one prefabricated hole (7, 6), which can be brought into registry by fitting the two capsule elements into one another, and
one of the at least one prefabricated hole (7) in an outer capsule element, is larger than the other of the at least one prefabricated hole (6), and/or is embodied as an oblong hole or an elliptical hole.

12. The system according to claim 1, wherein the capsule elements are made from polyethylene, polycarbonate, polyester, polypropylene or polyethylene terephthalate, in an injection moulding process and the at least one prefabricated hole (6, 7) are formed in the same injection moulding process.

13. The system according to claim 1, wherein the air outlet representing an opening in the center of the end of the mouthpiece (78) that is next to the mouth during use.

14. The system according to claim 1 wherein: the inhaler comprises the mouthpiece (78) with one end that is closest to a mouth of a user during use and forms an opening that is connected to the capsule chamber (74) in a middle of a mouth end, and a component that forms the capsule receptacle (173a) is embodied as a cap which, in a transporting state of the system, closes off the opening at the mouth end.

15. The system according to claim 14, wherein the cap closes off the opening at the mouth end in such a way that the areas to which a user places his lips when using the inhaler are covered.

16. The system according to claim 1, wherein a component that forms the capsule receptacle (173a) comprises elements which prevent the capsule receptacle (173a) from being non-destructively reinserted in the capsule chamber (74) after being fully removed from the capsule chamber (74).

17. The system according to claim 16, wherein the elements include spring arms which prevent the capsule receptacle (173a) from being non-destructively reinserted in the capsule chamber (74) after being fully removed from the capsule chamber (74).

18. The system according to claim 1, wherein the capsule receptacle (173a) is formed by a thermoformed film or blister film.

19. The system according to claim 1, wherein the inhaler comprises a body (100) forming the capsule chamber (74), which is formed by two parts, preferably in the form of halves, which are joined together by a joint formed by welding, lamination, gluing or sealing.

20. The system according to claim 1 wherein the inhaler comprises a body (100) forming the capsule chamber (74) which consists essentially of a thermoformed film or blister film.

21. The system according to claim 1, wherein:
the capsule is located in the inhaler in a transporting state of the system,
the capsule (71) comprises at least one prefabricated hole (72, 72a, 72b), the capsule receptacle (173a) comprises or is formed by, an extensible and/or flexible film, which film at least partially surrounding the capsule such that in the transporting state of the system the film closes off the at least one prefabricated hole (72, 72a, 72b) and/or all the holes in the capsule (71), part of the film protrudes beyond the capsule (71) at one end of the capsule (71) and/or the film is connected to a pull strip, and the inhaler comprises an opening or an opening can be exposed on the inhaler, and the film can be pulled out of the inhaler by its protruding part and/or by its pull strip through the opening, whereupon the at least one prefabricated hole (72, 72a, 72b) and/or all the holes on the capsule (11, 74) are exposed.

22. The system comprising the inhaler and capsule according to claim 1, wherein two capsules (71) belong to the system and the inhaler comprises two capsule chambers (74) and two capsule receptacles (173a).

23. The system comprising the inhaler and two capsules according to claim 22, wherein the two capsules are filled with different formulations and/or different amounts of formulation.

24. A method for using a system comprising an inhaler and capsule according to claim 1, wherein the capsule receptacle (173a) which is part of a pulling element (173) or is formed by a pulling element (173) with a powder-filled, pre-perforated capsule (71) contained therein, is assembled with the other components of the inhaler, the part of the capsule receptacle (173a) that holds the capsule (71) being arranged in the capsule chamber (74) of the inhaler, after the assembly of the components of the inhaler, the system is in a state that is suitable for transportation or storage, in which the holes of the capsule (71) formed by the capsule body (2) and capsule cap (1) are closed off, and comprising the step of converting the system into a state ready for use by pulling the pulling element (173), such that the pulling exposes the holes of the capsule.

25. The method according to claim 24, wherein the inhaler comprises a body (100) forming the capsule chamber (74), which is formed by two parts preferably in the form of halves, the capsule receptacle (173a) with the capsule (71) initially being placed in the first part of the body (100) in place of the capsule chamber (74), then the capsule chamber (74) being completed by the placement of the second part of the body (100) and the two parts of the body (100) being joined together by welding, laminating, gluing or sealing.

26. The method according to claim 25, wherein before the capsule receptacle (173a) is assembled with other components of the inhaler, firstly the capsule body (2) being open at one end is inserted in the capsule receptacle (173a), the capsule body (2) is filled with a measured amount of preferably powdered pharmaceutical preparation, and secondly the capsule body is then closed off with a capsule cap (1).

27. The system of claim 1, wherein the reservoir contains the pharmaceutical in the form of a powdered pharmaceutical preparation, which is nebulised by the Bernoulli effect when the inhaler is used.

28. The system according to claim 1, wherein the pharmaceutical is a powdered preparation.

* * * * *